(12) United States Patent
Semenyuk

(10) Patent No.: US 11,347,704 B2
(45) Date of Patent: May 31, 2022

(54) BIOLOGICAL GRAPH OR SEQUENCE SERIALIZATION

(71) Applicant: Seven Bridges Genomics Inc., Cambridge, MA (US)

(72) Inventor: Vladimir Semenyuk, Pacific Grove, CA (US)

(73) Assignee: Seven Bridges Genomics Inc., Charlestown, MA (US)

(*) Notice: Subject to any disclaimer, the term of this patent is extended or adjusted under 35 U.S.C. 154(b) by 1087 days.

(21) Appl. No.: 14/885,192

(22) Filed: Oct. 16, 2015

(65) Prior Publication Data

US 2017/0109383 A1 Apr. 20, 2017

(51) Int. Cl.
*G06F 16/22* (2019.01)
*G06F 16/901* (2019.01)
(Continued)

(52) U.S. Cl.
CPC .... *G06F 16/2219* (2019.01); *G06F 16/24568* (2019.01); *G06F 16/9024* (2019.01);
(Continued)

(58) Field of Classification Search
CPC ......... G06F 17/30318; G06F 17/30516; G06F 17/30958; G06F 19/10; G06F 16/2219;
(Continued)

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| KR | 101282798 B1 | 7/2013 |
| TW | 201243117 A | 11/2012 |

(Continued)

OTHER PUBLICATIONS

Title: Serialization (C#) Publisher Microsoft knowledgebase, Last Updated Date: Jan. 2, 2020 URL: https://docs.microsoft.com/en-us/dotnet/csharp/programming-guide/concepts/serialization/ (Year: 2020).*

(Continued)

*Primary Examiner* — Ashish Thomas
*Assistant Examiner* — Abdullah A Daud
(74) *Attorney, Agent, or Firm* — Wolf, Greenfield & Sacks, P.C.

(57) ABSTRACT

Methods of the invention include representing biological data in a memory subsystem within a computer system with a data structure that is particular to a location in the memory subsystem and serializing the data structure into a stream of bytes that can be deserialized into a clone of the data structure. In a preferred genomic embodiment, the biological data comprises genomic sequences and the data structure comprises a genomic directed acyclic graph (DAG) in which objects have adjacency lists of pointers that indicate the location of any object adjacent to that object. After serialization and deserialization, the clone genomic DAG has the same structure as the original to represent the same sequences and relationships among them as the original.

13 Claims, 20 Drawing Sheets

(51) Int. Cl.

| | |
|---|---|
| *G06F 16/2455* | (2019.01) |
| *G16B 50/00* | (2019.01) |
| *G16B 50/20* | (2019.01) |
| *G16B 30/10* | (2019.01) |
| *G16B 50/30* | (2019.01) |
| *G16B 50/10* | (2019.01) |
| *G16B 50/50* | (2019.01) |
| *G16B 30/00* | (2019.01) |

(52) U.S. Cl.
CPC ............ *G16B 30/10* (2019.02); *G16B 50/00* (2019.02); *G16B 50/10* (2019.02); *G16B 50/20* (2019.02); *G16B 50/30* (2019.02); *G16B 50/50* (2019.02); *G16B 30/00* (2019.02)

(58) Field of Classification Search
CPC ........... G06F 16/24568; G06F 16/9024; G16B 30/10; G16B 50/30; G16B 50/50; G16B 50/10; G16B 50/20; G16B 50/00; G16B 30/00
USPC ......................................................... 707/336
See application file for complete search history.

(56) References Cited

U.S. PATENT DOCUMENTS

| | | | |
|---|---|---|---|
| 4,988,617 A | 1/1991 | Landegren et al. | |
| 5,234,809 A | 8/1993 | Boom et al. | |
| 5,242,794 A | 9/1993 | Whiteley et al. | |
| 5,494,810 A | 2/1996 | Barany et al. | |
| 5,511,158 A | 4/1996 | Sims | |
| 5,583,024 A | 12/1996 | McElroy et al. | |
| 5,674,713 A | 10/1997 | McElroy et al. | |
| 5,700,673 A | 12/1997 | McElroy et al. | |
| 5,701,256 A | 12/1997 | Marr et al. | |
| 6,054,278 A | 4/2000 | Dodge et al. | |
| 6,210,891 B1 | 4/2001 | Nyren et al. | |
| 6,223,128 B1 | 4/2001 | Allex et al. | |
| 6,306,597 B1 | 10/2001 | Macevicz | |
| 6,567,861 B1* | 5/2003 | Kasichainula | G06F 9/548 |
| | | | 709/246 |
| 6,582,938 B1 | 6/2003 | Su et al. | |
| 6,627,887 B1* | 9/2003 | Dudley | G01N 23/2251 |
| | | | 250/306 |
| 6,818,395 B1 | 11/2004 | Quake et al. | |
| 6,828,100 B1 | 12/2004 | Ronaghi | |
| 6,833,246 B2 | 12/2004 | Balasubramanian | |
| 6,890,763 B2 | 5/2005 | Jackowski et al. | |
| 6,911,345 B2 | 6/2005 | Quake et al. | |
| 6,925,389 B2 | 8/2005 | Hitt et al. | |
| 6,989,100 B2 | 1/2006 | Norton | |
| 7,169,560 B2 | 1/2007 | Lapidus et al. | |
| 7,232,656 B2 | 6/2007 | Balasubramanian et al. | |
| 7,282,337 B1 | 10/2007 | Harris | |
| 7,321,623 B2 | 1/2008 | Dambrackas | |
| 7,483,585 B2 | 1/2009 | Brakus, Jr. | |
| 7,577,554 B2 | 8/2009 | Lystad et al. | |
| 7,580,918 B2 | 8/2009 | Chang et al. | |
| 7,598,035 B2 | 10/2009 | Macevicz | |
| 7,620,800 B2 | 11/2009 | Huppenthal et al. | |
| 7,776,616 B2 | 8/2010 | Heath et al. | |
| 7,809,509 B2 | 10/2010 | Milosavljevic | |
| 7,835,871 B2 | 11/2010 | Kain et al. | |
| 7,885,840 B2 | 2/2011 | Sadiq et al. | |
| 7,917,302 B2 | 3/2011 | Rognes | |
| 7,957,913 B2 | 6/2011 | Chinitz et al. | |
| 7,960,120 B2 | 6/2011 | Rigatti et al. | |
| 8,146,099 B2 | 3/2012 | Tkatch et al. | |
| 8,165,821 B2 | 4/2012 | Zhang | |
| 8,209,130 B1 | 6/2012 | Kennedy et al. | |
| 8,340,914 B2 | 12/2012 | Gatewood et al. | |
| 8,370,079 B2 | 2/2013 | Sorenson et al. | |
| 8,639,847 B2 | 1/2014 | Blaszczak et al. | |
| 8,972,201 B2 | 3/2015 | Mande et al. | |
| 9,063,914 B2 | 6/2015 | Kural et al. | |
| 9,092,402 B2 | 7/2015 | Kural et al. | |
| 9,116,866 B2 | 8/2015 | Kural | |
| 9,390,226 B2 | 7/2016 | Kural | |
| 9,501,334 B2* | 11/2016 | Fink | G06F 9/546 |
| 9,817,944 B2 | 11/2017 | Kural | |
| 10,204,207 B2* | 2/2019 | Kural | G16H 50/00 |
| 2002/0164629 A1 | 11/2002 | Quake et al. | |
| 2002/0190663 A1 | 12/2002 | Rasmussen | |
| 2004/0023209 A1 | 2/2004 | Jonasson | |
| 2004/0261008 A1* | 12/2004 | Pepin | G06F 9/4492 |
| | | | 715/234 |
| 2005/0089906 A1 | 4/2005 | Furuta et al. | |
| 2006/0024681 A1 | 2/2006 | Smith et al. | |
| 2006/0195269 A1 | 8/2006 | Yeatman et al. | |
| 2006/0292611 A1 | 12/2006 | Berka et al. | |
| 2007/0114362 A1 | 5/2007 | Feng et al. | |
| 2007/0166707 A1 | 7/2007 | Schadt et al. | |
| 2008/0003571 A1 | 1/2008 | McKernan et al. | |
| 2008/0077607 A1 | 3/2008 | Gatawood et al. | |
| 2008/0162552 A1* | 7/2008 | Bonev | G06F 8/75 |
| 2008/0189352 A1* | 8/2008 | Mitchell | H04L 1/1809 |
| | | | 709/201 |
| 2008/0251711 A1 | 10/2008 | Reilly | |
| 2008/0281463 A1 | 11/2008 | Suh et al. | |
| 2008/0294403 A1 | 11/2008 | Zhu et al. | |
| 2009/0026082 A1 | 1/2009 | Rothberg et al. | |
| 2009/0119313 A1 | 5/2009 | Pearce | |
| 2009/0127589 A1 | 5/2009 | Rothberg et al. | |
| 2009/0164135 A1 | 6/2009 | Brodzik et al. | |
| 2009/0191565 A1 | 7/2009 | Lapidus et al. | |
| 2009/0233809 A1 | 9/2009 | Faham et al. | |
| 2009/0300781 A1 | 12/2009 | Bancroft et al. | |
| 2009/0318310 A1 | 12/2009 | Liu et al. | |
| 2009/0325145 A1 | 12/2009 | Sablon et al. | |
| 2010/0010992 A1 | 1/2010 | Morris | |
| 2010/0024030 A1* | 1/2010 | Meijer | G06F 16/90344 |
| | | | 726/18 |
| 2010/0035252 A1 | 2/2010 | Rothberg et al. | |
| 2010/0041048 A1 | 2/2010 | Diehl et al. | |
| 2010/0079462 A1* | 4/2010 | Breeds | G06T 11/206 |
| | | | 345/440 |
| 2010/0137143 A1 | 6/2010 | Rothberg et al. | |
| 2010/0169026 A1* | 7/2010 | Sorenson | G16B 30/00 |
| | | | 702/20 |
| 2010/0188073 A1 | 7/2010 | Rothberg et al. | |
| 2010/0197507 A1 | 8/2010 | Rothberg et al. | |
| 2010/0240046 A1 | 9/2010 | Palmer et al. | |
| 2010/0282617 A1 | 11/2010 | Rothberg et al. | |
| 2010/0285578 A1 | 11/2010 | Selden et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2011/0004413 A1 | 1/2011 | Carnevali et al. | |
| 2011/0009278 A1 | 1/2011 | Kain et al. | |
| 2011/0096193 A1 | 4/2011 | Egawa | |
| 2011/0098193 A1 | 4/2011 | Kingsmore et al. | |
| 2011/0207135 A1 | 8/2011 | Faham et al. | |
| 2011/0257889 A1 | 10/2011 | Klammer et al. | |
| 2012/0004111 A1* | 1/2012 | Colwell | G16B 40/20 |
| | | | 506/2 |
| 2012/0030566 A1 | 2/2012 | Victor | |
| 2012/0040851 A1 | 2/2012 | Lieberman et al. | |
| 2012/0041727 A1 | 2/2012 | Mishra et al. | |
| 2012/0045771 A1 | 2/2012 | Beier et al. | |
| 2012/0157322 A1 | 6/2012 | Myllykangas et al. | |
| 2012/0239706 A1 | 9/2012 | Steinfadt | |
| 2012/0330566 A1 | 12/2012 | Chaisson | |
| 2013/0029879 A1 | 1/2013 | Shetty et al. | |
| 2013/0035904 A1 | 2/2013 | Kuhn | |
| 2013/0059738 A1 | 3/2013 | Leamon et al. | |
| 2013/0059740 A1 | 3/2013 | Drmanac et al. | |
| 2013/0073214 A1 | 3/2013 | Hyland et al. | |
| 2013/0124100 A1 | 5/2013 | Drmanac et al. | |
| 2013/0124573 A1* | 5/2013 | Seth | G06F 9/4493 |
| | | | 707/798 |
| 2013/0232480 A1 | 9/2013 | Winterfeldt et al. | |
| 2013/0289099 A1 | 10/2013 | Goff et al. | |

(56) References Cited

U.S. PATENT DOCUMENTS

| | | |
|---|---|---|
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0025312 A1* | 1/2014 | Chin ............... G16B 20/00 702/20 |
| 2014/0051588 A9 | 2/2014 | Drmanac et al. |
| 2014/0066317 A1 | 3/2014 | Talasaz |
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0281708 A1 | 9/2014 | Adam et al. |
| 2014/0323320 A1 | 10/2014 | Jia et al. |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0094212 A1 | 4/2015 | Gottimukkala et al. |
| 2015/0110754 A1 | 4/2015 | Bai et al. |
| 2015/0112602 A1* | 4/2015 | Kural ............... G16B 30/00 702/19 |
| 2015/0112658 A1 | 4/2015 | Kural et al. |
| 2015/0186683 A1* | 7/2015 | Fiske ............... G06F 9/448 726/26 |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1* | 7/2015 | Kural ............... G16B 30/00 702/19 |
| 2015/0227685 A1* | 8/2015 | Kural ............... C12Q 1/6883 702/19 |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0331728 A1* | 11/2015 | Kim ............... G06F 3/0482 719/319 |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0057226 A1* | 2/2016 | Bestler ............... H04L 67/1095 709/217 |
| 2016/0147748 A1* | 5/2016 | Florendo ............ G06F 16/2282 707/809 |
| 2016/0259880 A1 | 9/2016 | Semenyuk |
| 2016/0306921 A1 | 10/2016 | Kural |
| 2016/0342737 A1* | 11/2016 | Kaye ............... G16B 30/00 |
| 2016/0350478 A1* | 12/2016 | Chin ............... G16B 30/10 |
| 2016/0364523 A1 | 12/2016 | Locke et al. |
| 2017/0046614 A1* | 2/2017 | Golovashkin ......... G06N 3/082 |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0058430 A1* | 3/2017 | Watts ............... C12Q 1/04 |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |
| 2019/0274311 A1* | 9/2019 | Harman ............... C05F 11/08 |

FOREIGN PATENT DOCUMENTS

| | | | |
|---|---|---|---|
| WO | WO2001035269 A2 * | 11/1999 | ............ G06F 3/016 |
| WO | WO2001035269 A2 * | 5/2001 | ............ G06F 3/016 |
| WO | 2007/086935 A2 | 8/2007 | |
| WO | 2010/010992 A1 | 1/2010 | |
| WO | 2011139797 A2 | 11/2011 | |
| WO | 2012/096579 A2 | 7/2012 | |
| WO | 2012/098515 A1 | 7/2012 | |
| WO | 2012/142531 A2 | 10/2012 | |
| WO | 2013/035904 A1 | 3/2013 | |
| WO | 2013043909 A1 | 3/2013 | |
| WO | 2013/106737 A1 | 7/2013 | |
| WO | 2013097257 A1 | 7/2013 | |
| WO | 2013184643 A1 | 12/2013 | |
| WO | 2015027050 A1 | 2/2015 | |
| WO | 2015048753 A1 | 4/2015 | |
| WO | 2015058093 A1 | 4/2015 | |
| WO | 2015058095 A1 | 4/2015 | |
| WO | 2015058097 A1 | 4/2015 | |
| WO | 2015058120 A1 | 4/2015 | |
| WO | 2015061099 A1 | 4/2015 | |
| WO | 2015061103 A1 | 4/2015 | |
| WO | 2015105963 A1 | 7/2015 | |
| WO | 2015123269 A1 | 8/2015 | |
| WO | 2016141294 A1 | 9/2016 | |
| WO | 2016201215 A1 | 12/2016 | |
| WO | 2017120128 A1 | 7/2017 | |
| WO | 2017123864 A1 | 7/2017 | |
| WO | 2017147124 A1 | 8/2017 | |

OTHER PUBLICATIONS

Ulrik Brandes, "Graph Markup Language (GraphML)", Published in 2010, ISBN 978-1-584-88412-5, (Year: 2010).*

"GraphML.py" source code listing from NetworkX project 2014 (Year: 2014).*

Albers et al., Dindel: Accurate indel calls from short-read data, 2011, pp. 961-973, vol. 21, Genome Research.

Albers, 2011, Dindel: Accurate indel calls from short-read data, Genome Research 21:961-973.

Brose et al., Cancer Risk Estimates for BRCA1 Mutation Carriers Identified in a Risk Evaluation Program, 2002, pp. 1365-1372, vol. 94, Journal of the National Cancer Institute.

Chen, 2014, Genome architecture and its role in human copy number variation, Genomics Inform 12(4):136-144.

Duan et al., Optimizing de novo common wheat transcriptome assembly using short-read RNA-Seq data. (2012) pp. 1-12, vol. 13, BMC Genomics.

EESR issued in EP 14837955.5.

EESR issued in EP 14847490.1.

EESR issued in EP 14854801.9.

Exam Report issued in EP14803268.3.

Friedman, The World is Flat, 2005, pp. 94-95, Farrar, Straus, and Giroux, New York.

International Search Report and Written Opinion dated Apr. 7, 2017, for International Patent Application No. PCT/US17/13329, filed Jan. 13, 2017 (9 pages).

International Search Report and Written Opinion dated Feb. 4, 2015, for International Patent Application No. PCT/US2014/061198, filed Oct. 17, 2014 (8 pages).

International Search Report and Written Opinion dated Feb. 10, 2015, for International Patent Application No. PCT/US2014/060690, filed Oct. 15, 2014 (11 pages).

ISR/Written Opinion issued for PCT/US2017/012015.

Koolen, 2008, Clinical and Molecular Delineation of the 17q21.31 Microdeletion Syndrome, J Med Gen 45(11):710-720.

Lee et al. Accurate read mapping using a graph-based human pan-genome. (May 2015) American Society of Human Genetics 64th Annual Meeting Platform Abstracts; Abstract 41.

Lee, 2014, Accurate read mapping using a graph-based human pan-genome, ASHG 2014 Abstracts.

Lupski, 2005, Genomic disorders: Molecular mechanisms for rearrangements and conveyed phenotypes, PLoS Genetics 1(6):e49.

Marth et al., A general approach to single-nucleotide polymorphism discovery, Dec. 1999, pp. 452-456, vol. 23, Nature Genetics.

Marth, 1999, A general approach to single-nucleotide polymorphism discovery, Nature Genetics 23:452-456.

Newman et al. An ultrasensitive method for quantitating circulating tumor DNA with broad patient coverage. Apr. 2014, pp. 1-22, vol. 20, No. 5, Nature Medicine.

Olsson et al. Serial monitoring of circulating tumor DNA in patients with primary breast cancer for detection of occult metastatic disease. May 2015, pp. 1034-1047, vol. 7, No. 8, EMBO Molecular Medicine.

(56) References Cited

OTHER PUBLICATIONS

Parks, 2015, Detecting non-allelic homologous recombination from high-throughput sequencing data, Genome Biol 16:17.
Pop et al., 2004, Comparative genome assembly, Briefings in Bioinformatics vol. 5, pp. 237-248.
Wheeler et al., The complete genome of an individual by massively parallel DNA sequencing, 2008, pp. 872-876, Nature.
Written Opinion issued in SG 11201601124Y.
Written Opinion issued in SG 11201602903X.
Written Opinion issued in SG 11201603039P.
Written Opinion issued in SG 11201605506Q.
Zhang et al., Construction of a high-density genetic map for sesame based on large scale marker development by specific length amplified fragment (SLAF) sequencing. (2013) pp. 1-12, vol. 13, BMC Plant Biology.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Hokamp, 2003, Wrapping up BLAST and Other Applications for Use on Unix Clusters, Bioinformatics 19(3)441-42.
Holland, 2008, BioJava: an open-source framework for bioinformatics, Bioinformatics 24(18):2096-2097.
Homer, 2010, Improved variant discovery through local re-alignment of short-read next generation sequencing data using SRMA, Genome Biol 11(10):R99.
Hoon, 2003, Biopipe: A flexible framework for protocol-based bioinformatics analysis, Genome Res 13(8):1904-1915.
Horspool, 1980, Practical Fast Searching in Strings, Software—Practice & Experience 10:501-506.
Huang, Chapter 3: Bio-Sequence Comparison and Alignment, ser. CurrTop Comp Mol Biol. Cambridge, Mass.: The MIT Press, 2002.
Hull, 2006, Taverna: a tool for building and running workflows of services, Nucl Acids Res 34(Web Server issue): W729-32.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated May 5, 2016, for International Patent Application No. PCT/US2016/020899, wiht International Filing Date Mar. 4, 2016 (12 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014 (22 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed October 215, 2014, (11 pages).
International Search Report and Written Opinion dated Sep. 2, 2016, for International Patent Application No. PCT/US2016/033201 with International Filing Date May 19, 2016 (14 pages).
International Search Report and Written Opinion dated Sep. 7, 2016, for International Application No. PCT/US2016/036873 with International filing date Jun. 10, 2016 (8 pages).
International Search Report and Written Opinion of the International Searching Authority dated Nov. 17, 2015 for International Application No. PCT/US2015/048891 (11 Pages).
Kano, 2010, Text mining meets workflow: linking U-Compare with Taverna, Bioinformatics 26(19):2486-7.
Katoh, 2005, MAFFT version 5: improvement in accuracy of multiple sequence alignment, Nucl Acids Res 33 (2):511-518.
Kawas, 2006, BioMoby extensions to the Taverna workflow management and enactment software, BMC Bioinformatics 7:523.
Kehr, 2014, Genome alignment with graph data structures: a comparison, BMC Bioinformatics 15:99.
Kent, 2002, BLAT-The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
Kumar, 2010, Comparing de novo assemblers for 454 transcriptome data, BMC Genomics 11:571.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Lanzen, 2008, The Taverna Interaction Service: enabling manual interaction in workflows, Bioinformatics 24 (8):1118-20.
Larkin, 2007, Clustal W and Clustal X version 2.0, Bioinformatics 23(21):2947-2948.
Layer, 2015, Efficient compression and analysis of large genetic variation datasets, Biorxiv preprint, available at http://biorxiv.org/content/early/2015/04/20/018259.
Layer, 2015, Efficient genotype compression and analysis of large genetic-variation data sets, Nat Meth 13(1):63-65.
Lee, 2002, Multiple sequence alignment using partial order graphs, Bioinformatics 18(3):452-464.
Lee, 2003, Generating consensus sequences from partial order multiple sequence alignment graphs, Bioinformatics 19 (8):999-1008.
International Search Report and Written Opinion dated Jan. 10, 2017, for application No. PCT/US16/57324 with International filing date Oct. 17, 2016 (7 pages).

(56) References Cited

OTHER PUBLICATIONS

Grasso, 2004, Combining partial order alignment and progressive multiple sequence alignment increases alignment speed and scalability to very large alignment problems, Bioinformatics 20(10):1546-1556.
Abouelhoda, 2012, Tavaxy: integrating Taverna and Galaxy workflows with cloud computing support, BMC Bioinformatics 13:77.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13):i352-i360.
Airoldi, 2008, Mixed membership stochastic blockmodels, JMLR 9:1981-2014.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioninformatics 29(10):1250-1259.
BCF2 Quick Reference (r198), available at http://samtools.github.io/hts-specs/BCFv2_qref.pdf.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages); retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.
Chen, 2012, Transient hypermutability, chromothripsis and replication-based mechanisms in the generation of concurrent clustered mutations, Mutation Res 750(1):562-59.
Chin, 2013, Nonhybrid finished microbial genome assemblies from long-read SMRT sequencing data, Nat Meth 10 (6):563-569.
Chuang, 2001, Gene recognition based on DAG shortest paths, Bioinformatics 17(Suppl. 1):s56-s64.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1:e167.
Cohen-Boulakia, 2014, Distilling structure in Taverna scientific workflows: a refactoring approach, BMC Bioinformatics 15(Suppl 1):S12.
Compeau, 2011, How to apply de Bruijn graphs to genome assembly, Nat Biotech 29(11):987-991.
Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Dudley, 2009, A quick guide for developing effective bioinformatics programming skills, PLoS Comput Biol 5(12):e1000589.
Durbin, 2014, Efficient haplotype matching and storage using the positional Burrows-Wheeler transform (PBWT), Bioinformatics 30(9): 1266-1272.
Durham, 2005, EGene: a configurable pipeline system for automated sequence analysis, Bioinformatics 21 (12):2812-2813.
Enedelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Glusman, 2014, Whole-genome haplotyping approaches and genomic medicine, Genome Med 6:73.
Goto, 2010, BioRuby: bioinformatics software for the Ruby programming language, Bioinformatics 26(20):2617-2619.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harenberg, 2014, Community detection in large-scale networks: a survey and empirical evaluation, WIREs Comp Stat 6:426-439.
Peixoto, 2014, Efficient Monte Carlo and greedy heuristic for the inference of stochastic block models, Phys. Rev. E 89, 012804.
Pope, 2014, ROVER Variant Caller: Read-Pair Overlap Considerate Variant-Calling Software Applied to PCR-Based Massively Parallel Sequencing Datasets, Source Code Bio Med 9:3.
Popitsch, 2013, NGC: lossless and lossy compression of aligned high-throughput sequencing data, Nucl Acids Res, 41(1):e27.
Posada, 1998, Model Test: testing the model of DNA substitution, Bioinformatics 14(9):817-8.
Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Rajaram, 2013, Pearl millet [*Pennisetum glaucum* (L.) R. Br.] consensus linkage map constructed using four RIL mapping populations and newly developed EST-SSRs, BMC Genomics 14(1):159.

(56) References Cited

OTHER PUBLICATIONS

Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Rothberg, 2011, An integrated semiconductor device enabling non-optical genome sequencing, Nature 475:348-352.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schenk, 2013, A pipeline for comprehensive and automated processing of electron diffraction data in IPLT, J Struct Biol 182(2):173-185.
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5)596-609.
Soni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav-integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing-pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tan, 2010, A Comparison of Using Taverna and BPEL in Building Scientific Workflows: the case of caGrid, Concurr Comput 22(9):1098-1117.
Tan, 2010, CaGrid Workflow Toolkit: aTaverna based workflow tool for cancer grid, BMC Bioinformatics 11:542.
Tarhio, 1993, Approximate Boyer-Moore String Matching, SIAM J Comput 22(2):243-260.
Tewhey, 2011, The importance of phase information for human genomics, Nat Rev Gen 12:215-223.
The 1000 Genomes Project, 2015, A global reference for human genetic variation, Nature 526:68-74.
The Variant Call Format (VCF) Version 4.2 Specification (Jan. 26, 2015), available at https://samtools.github.io/hts-specs/VCFv4.2.pdf.
Thomas, 2014, Community-wide effort aims to better represent variation in human reference genome, Genome Web (11 pages).
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Lee, 2005, Bioinformatics analysis of alternative splicing, Brief Bioinf 6(1):23-33.
Lee, 2014, Mosaik: A hash-based algorithm for accurate next-generation sequencing short-read mapping, PLoS One 9(3):e90581.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, A survey of sequence alignment algorithms for next-generation sequencing, Briefings in Bionformatics 11(5):473-483.
Li, 2015, BGT: efficient and flexible genotype query across many samples, arXiv: 1506.08452 [q-bio.GN].
Li, 2015, Towards Better Understanding of Artificats in Variant Calling from High-Coverage Samples, arXiv:1404.0929 [q-bio.GN].
Life Technologies, 2013, Rapid Exome Sequencing Using the Ion Proton System and Ion Ampliseq Technology, Application Note (5 Pages).

(56) References Cited

OTHER PUBLICATIONS

Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6(4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Rawe, 2013, Low Concordance of Multiple Variant-Calling Pipelines: Practical Implications for Exome and Genome Sequencing, Genome Med 5:28.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation: Practice and Experience 18(10):1067-1100.
Oshlack, 2010, From RNA-seq reads to differential expression results. Genome Bio 11:220.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Alioto et al., A comprehensive assessment of somatic mutation detection in cancer using whole-genome sequencing, Nature Communications, Dec. 9, 2015.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG); simulating sequence evolution, 2005, pp. iii31-iii38, vol. 21, Oxford University Press.
Craig, 1990, Ordering of cosmid clones covering the Herpes simplex virus type I (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
Examination Report issued in SG 11201601124Y.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
International Search Report and Written Opinion dated Aug. 31, 2017, for International Application No. PCT/US2017/018830 with International Filing Date Feb. 22, 2017, (11 pages).
Lecca, 2015, Defining order and timing of mutations during cancer progression: the TO-DAG probabilistic graphical model, Frontiers in Genetics, vol. 6 Article 309 1-17.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pages ii79-ii85, vol. 21.
Pruesse, 2012, SINA: Accurate high-throughput multiple sequence alignment of ribosomal RNA genes, Bioinformatics 28:14 1823-1829.
Sturgeon, RCDA: a highly sensitive and specific alternatively spliced transcript assembly tool featuring upstream consecutive exon structures, Genomics, Dec. 2012, 100(6): 357-362.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Written Opinion issued in SG 11201603044S.
Zeng, 2013, PyroHMMvar: a sensitive and accurate method to call short indels and SNPs for Ion Torrent and 454 data, Bioinformatics 29:22 2859-2868.

\* cited by examiner

FIG. 8

BIOLOGICAL GRAPH OR SEQUENCE SERIALIZATION

TECHNICAL FIELD

The invention relates to systems and methods for serializing and deserializing data structures containing bioinformatic data.

BACKGROUND

Studying genomes can potentially reveal many insights into the health and history of organisms and entire species. Researchers can identify genes associated with cancer and other diseases through genomic studies, and genomics also plays an important role in forensics, genealogy, and agriculture, among other fields. A frequent approach to genomic studies includes sequencing DNA from a sample and comparing the resulting sequence reads to each other or to a known reference to characterize the genomes of organisms represented in the sample. Reference genomes often include whole genomes that have been sequenced and published, often available online. For example, Ensembl is a scientific project that aims to provide a centralized resource for geneticists in the form of a database and genome browser for the retrieval of genomic information. In the Ensembl project, sequence reads are fed into the system wherein they can be mapped to one of many reference genomes and stored as an SQL database for subsequent analysis and display.

Unfortunately, existing approaches to structuring genomic sequences into databases restrict the flexibility of those resources. Some database implementations are linked into their computer hardware in such a way that it is not possible to simply copy all or part of the database to another computer to use in analysis. Moreover, unlike flat-file database that contain simple, linear text for sequence entries, many algorithms used in genomic analysis structure data in memory as bifurcating or reticulated networks of pointers or references. For example, suffix trees and directed acyclic graphs are used to represent biological data, but implementations of those may not only use native pointers, which can't be directly copied to other systems, but may further include complex internal relationships or dependencies that present substantial challenges to moving or copying.

SUMMARY

Where biological information is represented with a data structure that is particular to a location in a computer system, methods of the invention are useful to send the information to a new location where the structure can be re-created so that the information can be accessed, used, or updated in the new location. Where a data structure includes features such as pointers or endianness that cannot simply be copied from one location in memory to another, the invention provides methods for serializing the structure into bytes that can be streamed. Methods are provided to deserialize the byte stream to create a clone of the data structure in the new location. Methods of the invention are applicable to graph data structures that represent entities and their connections using nodes and edges, which may be implemented using pointers to specific locations in memory.

Graph data structures may represent such biological information as protein interaction networks, multiple sequence alignments, gene ontologies, or phylogenetic trees, among others. Those graphs offer important benefits. For example, they may be queried particularly rapidly when the connections among nodes are represented using pointers in memory such that a processor can traverse a path through the graph by, starting at one node or edge object, reading from a pointer a location in memory of an adjacent object, and reading from the adjacent object by going directly to that location. Since pointers identify a specific physical location in memory, it may not be possible to simply copy the data structure to a new location. Not only would the pointer values be rendered a nullity in the new location, it is no trivial matter to update them during a copy operation due to the interconnectedness of the graph. An object's specific location is not known until it is created in the new location, but a pointer cannot be created until the new location to which it points is known. Such difficulties arise since graphs are not serial in nature. Since graphs are not serial data structures, they cannot be copied and recreated in any arbitrary fashion.

Additionally, different computer systems read bits from memory differently. For example, some systems are said to be big endian while some are little endian depending on whether values are stored at multiple addresses with the smallest address being used for the most significant or the least significant byte of the value. Like pointers, endianness is particular to a location in memory and cannot reliably be copied to new locations.

Using systems and methods of the invention, a data structure representing biological information can be serialized and streamed from its location to a new location. The serialization may include transforming the data into a series of containers that represent the data in a linear fashion conducive to being streamed to a different location. The serialization may be used to transfer the biological information and its structured representation between RAM and non-volatile memory, or from one storage medium to another, for example. Methods of the invention include deserializing the byte stream to build a clone of the biological information and its data structure. The data structure of the clone is particular to a new location, e.g., within the memory of a second computer system. The new data structure is a clone of the original in that it offers the same functionality, the same read/write access, and represents the same biological information as the original. However, location-specific features of the data structure such as pointers, references, or endianness are particular to the new location. Thus, algorithms used in genomic analysis that structure data in memory as bifurcating or reticulated networks of pointers or references are not limited in their flexibility of use.

A biological database, such as a database of genomic sequences, can be passed between client and server easily, or moved—partially or wholly—into RAM for certain manipulations and moved back into non-volatile memory for storage. Analytical tools created on one machine or platform can be transferred to others. The serialization and deserialization may be applied to a variety of different bioinformatic systems and may find particular applicability to the use of a directed acyclic graph (DAG) to represent homologous sequences such as protein or genomic sequences. Thus analytical tools can be made that have applications in variant discovery, sequence read assembly, read mapping, identification of unknown organisms, among many others, and those tools need not be locked into a particular system. This allows, for example, a service provider to implement a structure such as a genomic DAG on a server computer, but then also allow an end-user to stream all or parts of the genomic DAG to his or her local computer. This can provide the end user with access to analytical tools even when offline. The arrangement may also have particular applicability with sensitive information. For example, a clinic may use an online genomic reference DAG for analysis of aggregate, anonymized sequence data, but may stream to itself a local clone of at least a portion of that DAG to analyze patient data behind a firewall.

Aspects of the invention provide a method of transferring biological data. The method includes representing biological data as a graph data structure in a memory subsystem within a computer system. The graph data structure has a graph geometry and graph content. The method further includes serializing the graph data structure by serializing the graph geometry and the graph content into a stream of bytes, wherein the stream of bytes can be deserialized into a clone of the graph data structure that represents the biological data. In some embodiments, the method includes serializing the graph geometry into a first stream of bytes, serializing the graph content into a second stream of bytes, and combining the first stream of bytes and the second stream of bytes into the stream of bytes. Serializing the graph geometry may include expressing the graph geometry as a list of statements describing a series of modifications to a linear graph. Optionally, serializing the graph geometry and the graph content further comprises creating a first container that includes the list of statements and a second container that includes the graph content.

In certain embodiments, the graph data structure comprises a directed graph and the biological data comprises one selected from the group consisting of a gene ontology; a protein interaction network; a phylogeny; a mutation database; and amino acid sequence data.

In a preferred embodiment, the biological data include sequences and the graph data structure is a directed acyclic graph (DAG). Preferably, the DAG comprises objects in the memory subsystem (e.g., in which each object comprises an adjacency list comprising pointers that indicate the location of any object adjacent to that object). Portions of the genomic sequences that match each other when aligned may be each represented by a single object and wherein each of the genomic sequences is represented by a path through the DAG.

The method may include sending the stream of bytes over a network to a user computer.

The computer system may be a server system with the method optionally including providing to the user computer software that allows a user to deserialize the stream of bytes and modify the clone. In some embodiments, the method includes deserializing the serialized graph data structure into the clone by creating a second graph data structure comprising the graph geometry and the graph content within a second memory subsystem of a second computer system.

In some aspects, the invention provides a system for transferring biological data. The system includes a processor coupled to a memory subsystem having stored therein a graph data structure representing biological data—the graph data structure comprising a graph geometry and graph content—and instructions executable by the processor to cause the system to serialize the graph data structure by serializing the graph geometry and graph content into a stream of bytes. The stream of bytes can be deserialized into a clone of the graph data structure that represents the biological data.

In some embodiments, the system serializes the graph geometry into a first stream of bytes, serializes the graph content into a second stream of bytes, and combines the first stream and the second stream into the stream of bytes. Serializing the graph geometry may include expressing the graph geometry as a list of statements describing a series of modifications to a linear graph. Serializing the graph geometry and graph content may involve creating within the memory subsystem a first container that includes the list of statements and a second container that includes graph content.

The graph data structure may a directed graph with the biological data being a gene ontology, a protein interaction network, a phylogeny, a mutation database, or amino acid sequence data. In a preferred embodiment, the biological data comprises genomic sequences and the graph data structure comprises a directed acyclic graph (DAG). Preferably, the DAG comprises objects in the memory subsystem (e.g., with each object comprising an adjacency list comprising pointers that indicate the location of any object adjacent to that object). Portions of the genomic sequences that match each other when aligned may be each represented by a single object and wherein each of the genomic sequences is represented by a path through the DAG. The system may be operable to send the stream of bytes over a network to a user compute and the stream of bytes can be deserialized by the user computer into the clone within a second memory subsystem of the user computer.

In certain aspects, the invention provides a method of transferring biological data, in which the method includes: representing genomic sequences as a directed acyclic graph (DAG) in a memory subsystem within a computer system— the DAG comprising a graph geometry and graph content; serializing the DAG into a stream of bytes by (i) expressing the graph geometry as a list of statements describing a series of modifications to a linear graph, (ii) creating a first container that includes the list of statements, and (iii) creating a second container that includes the graph content; and deserializing the stream of bytes into a clone of the DAG that represents the biological data by (i) creating a second DAG by creating a linear graph and modifying it according to the list of statements, and (ii) populating the second DAG with the graph content.

In certain aspects, the invention provides a method of biological analysis. Methods include representing biological data as a data structure in a memory subsystem within a computer system and serializing the data structure into a stream of bytes, wherein the stream of bytes can be deserialized into a clone of the data structure that represents the biological data.

The data structure may be a directed graph and any suitable biological data may be included such as a gene ontology, a protein interaction network, a phylogeny, a mutation database, or amino acid sequence data. In a preferred genomic embodiment, the biological data comprises genomic sequences and the data structure comprises a directed acyclic graph (DAG). The DAG comprises objects in the memory subsystem, wherein each object comprises an adjacency list comprising pointers that indicate the location of any object adjacent to that object. Portions of the genomic sequences that match each other when aligned are each represented by a single object and each of the genomic sequences is represented by a path through the DAG.

In some embodiments, serializing the DAG comprises expressing a geometry of the DAG as a list of statements describing a series of modifications to a linear graph. Additionally, serializing the DAG may include creating a first container that includes the list of statements and a second container that includes content from the DAG.

In certain inter-system embodiments, methods of the invention include sending the stream of bytes over a network to a user computer. For example, the computer system may be a server system, and the method may include providing to the user computer software that allows a user to deserialize the stream of bytes and modify the clone. Thus the method may include deserializing the DAG into the clone within a second memory subsystem of a second computer system. In such embodiments, the first memory subsystem and the second memory subsystem may have different endianness.

In other intra-system embodiments, methods may include deserializing the DAG into the clone within a second memory subsystem of the computer system. For example, the memory subsystem may include RAM and the second memory subsystem may comprise a non-volatile computer-readable storage medium wherein the clone is stored. Additionally or alternatively, the memory subsystem may include a non-volatile computer-readable storage medium and the second memory subsystem may comprise RAM wherein the clone is stored.

In the preferred genomic embodiment, methods include obtaining sequence reads from nucleic acid from a sample, finding alignments between the sequence reads and paths through the DAG, and updating the DAG to represent a nucleic acid sequence from the sample. Finding alignments between the sequence reads and paths through the DAG may comprise a multi-dimensional look-back operation to find a highest-scoring trace through a multi-dimensional matrix. Where the genomic sequences are from a population of organisms, the method may include depicting at least a portion of the DAG to illustrate genetic diversity within the population.

In related aspects, the invention provides a system for biological analysis. The system includes a processor coupled to a memory subsystem. Stored in the memory subsystem are a data structure representing biological data and instructions executable by the processor to cause the system to serialize the data structure into a stream of bytes. The stream of bytes can be deserialized into a clone of the data structure that represents the biological data. The data structure may include a directed graph and the biological data may be, for example, a gene ontology, a protein interaction network, a phylogeny, a mutation database, or amino acid sequence data. In a preferred embodiment, the biological data comprises genomic sequences and the data structure is a directed acyclic graph (DAG). The DAG may include objects in the memory subsystem, and each object may include an adjacency list of pointers that indicate the location of any object adjacent to that object. By virtue of the DAG, portions of the clone genomic sequences that match each other when aligned may be each represented by a single one of the objects and each of the genomic sequences may be represented by a path through the DAG.

In some embodiments, serializing the DAG includes expressing a geometry of the DAG as a list of statements describing a series of modifications to a linear graph. This may include creating within the memory subsystem a first container that includes the list of statements and a second container that includes content from the DAG.

In intersystem embodiments, the system is operable to send the stream of bytes over a network to a user computer. The stream of bytes may be deserialized by the user computer into the clone within a second memory subsystem of the user computer.

In intra-system embodiments, the system is operable transfer the data structure between RAM and non-volatile memory of the memory subsystem by serializing the data structure into the stream of bytes and deserialize the stream of bytes into the clone.

BRIEF DESCRIPTION OF THE DRAWINGS

FIG. 8 shows the matrices used in the DAG alignment.

DETAILED DESCRIPTION

Figure 1:
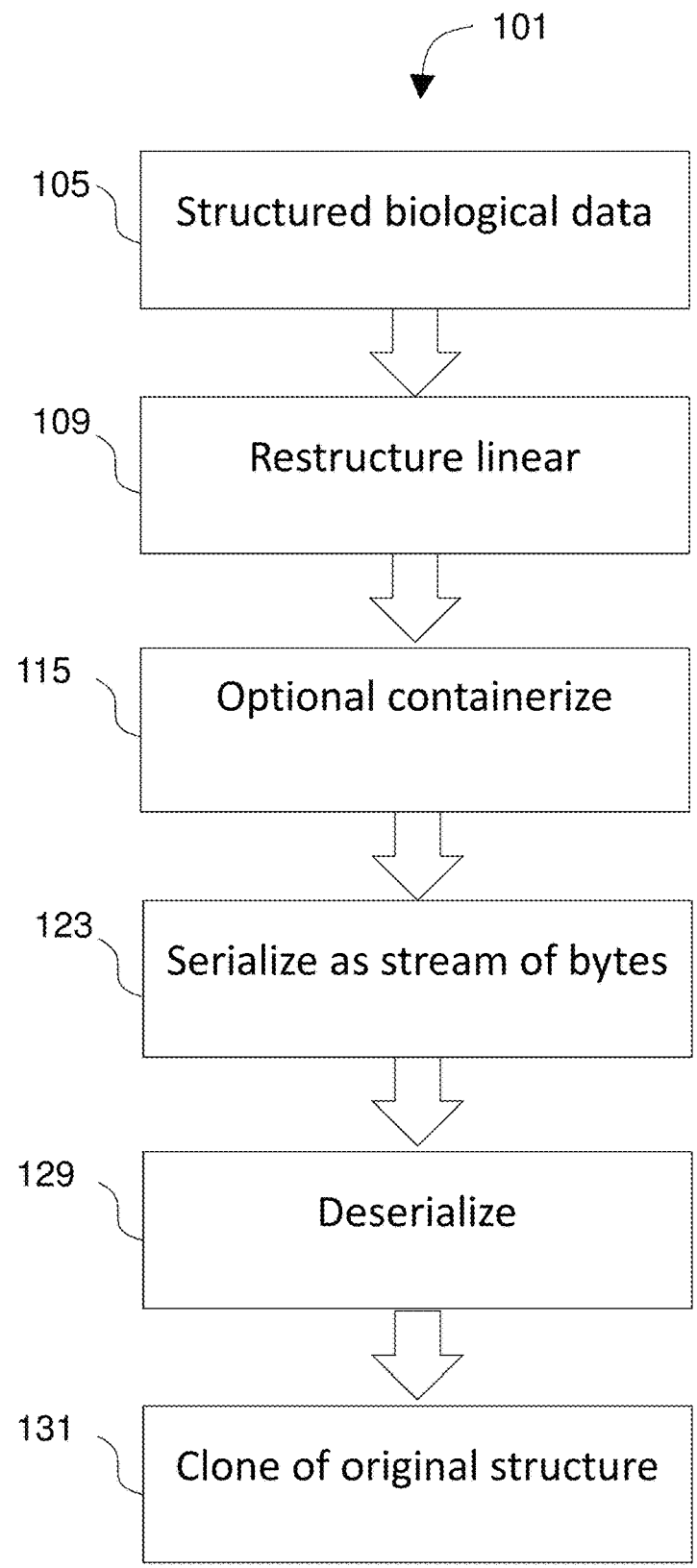
FIG. 1 illustrates a method of biological analysis.

Where biological information is represented with a data structure that is particular to a location in a computer system, methods of the invention can be used to send the information to a new location where the structure can be re-created so that the information can be accessed, used, or updated in the new location. Where a data structure includes features, such as pointers or endianness, that cannot simply be copied from one location in memory to another, the invention provides methods for serializing the structure into bytes that can be streamed.

Methods of the invention address problems that arise with existing and prospective data structures as those data structures are instantiated within a computing environment.

There is, in general, no reason to believe that a data structure, as actually instantiated in a computer during the execution of a program, will exist in a form that is amenable to storage, transmission, or description. These instantiations, rather, will in general reflect extreme path-dependency and will be scattered across several locations in one or several memory devices within one or several computers.

Even if it were easy to find those locations in memory, it may still be difficult to separate the essential information—that is, the biological information that the data structure is meant to represent—from accidental features of that particular instantiation of the data structure.

This problem may be addressed by serialization according to methods of the invention. One goal of serialization is to represent data in a faithful, compact, and linear way. Serialization is particularly urgent and particularly difficult when the data in question (1) are not intrinsically structured in a linear way and (2) are sufficiently large that even small inefficiencies in its representation will cause important real-world inefficiencies in storage, loading, and transmission.

Bioinformatic data exemplify both intrinsically non-linear data and data that amass in such quantities that even small inefficiencies in representation cause real problems in storage, loading, and transmission. One example of non-linear and massive bioinformatic data that is used in this disclosure relates to the use of graph representations of sequence data.

For example, U.S. Pat. Nos. 9,092,402; 9,063,914; 9,116,866; U.S. Pub. 2015/0199475 A1; U.S. Pub. 2015/0199474 A1; U.S. Pub. 2015/0197815 A1; U.S. Pub. 2015/0199472 A1; U.S. Pub. 2015/0199473 A1; U.S. Pub. 2015/0066381 A1; U.S. Pub. 2015/0227685 A1; and U.S. Pub. 2015/0057946 A1—the contents of each of which are incorporated by reference—all describe the benefits of graph representations of bioinformatic data, and the enormity of current and future bioinformatic data sets is well known. The present invention addresses problems associated with data structures for biological data and provides methods for serializing graph-based bioinformatic data. In particular graph-based genomes may be compressed and serialized according to methods described herein. To illustrate the compression and serialization of graph genomes, graph genomes are first briefly introduced and their use in genomics is shown through illustrative examples in connection with FIGS. 2-9.

FIG. 1 illustrates a method 101 of biological analysis. The method 101 includes representing 105 biological data as a data structure in a memory subsystem within a computer system. The data structure is re-structured 109 into a linear format. Any suitable operation can be performed to restructure the data. In a preferred embodiment, the data structure is expressed as a sequence of statements that, taken sequentially, describe the structure and content of the data structure. It may be preferable to containerize 115 the data. That is, the sequence of statements may be encapsulated within containers to create a certain format and aid a serialization or deserialization module in recognizing and working with the data. Method 101 includes serializing 123 the data structure into a stream of bytes. In method 101, the stream of bytes can be deserialized 129 to build 131 a clone of the data structure that represents the biological data. The represented 105 data structure may be a directed graph and any suitable biological data may be included such as a gene ontology, a protein interaction network, a phylogeny, a mutation database, or amino acid sequence data.

In a preferred genomic embodiment, the method 101 is a method for genomic analysis, the biological data comprises genomic sequences, and the data structure comprises a directed acyclic graph (DAG). In the preferred genomic embodiment, the DAG comprises objects in the memory subsystem, and each object is associated with an adjacency list or the DAG uses index-free adjacency and the DAG includes pointers that indicate the location of any object adjacent to that object. Portions of the genomic sequences that match each other when aligned are each represented by a single object and each of the genomic sequences is represented by a path through the DAG.

In some embodiments, serializing the DAG comprises expressing a geometry of the DAG as a list of statements describing a series of modifications to a linear graph. Additionally, serializing the DAG may include creating a first container that includes the list of statements and a second container that includes content from the DAG.

In certain inter-system embodiments, method 101 includes sending 123 the stream of bytes over a network to a user computer. For example, the computer system may be a server system, and the method 101 may include providing to the user computer software that allows a user to deserialize the stream of bytes and modify the clone. Thus method 101 may include deserializing the DAG into the clone within a second memory subsystem of a second computer system. In such embodiments of method 101, the first memory subsystem and the second memory subsystem may have different endianness.

In other intra-system embodiments, method 101 may include deserializing 129 the DAG into a clone within a second memory subsystem of the computer system. For example, the memory subsystem may include RAM and the second memory subsystem may comprise a non-volatile computer-readable storage medium wherein the clone is stored. Additionally or alternatively, the memory subsystem may include a non-volatile computer-readable storage medium and the second memory subsystem may comprise RAM wherein the clone of the DAG is stored. In the preferred genomic embodiment, the DAG is a genomic reference DAG used in DNA sequencing applications, in which the genomic reference DAG is a tool for sequence read mapping, assembly, and analysis. Methods of the invention may include obtaining sequence reads from nucleic acid from a sample, finding alignments between the sequence reads and paths through the DAG, and updating the DAG to represent a nucleic acid sequence from the sample. Finding alignments between the sequence reads and paths through the DAG may comprise a multi-dimensional look-back operation to find a highest-scoring trace through a multi-dimensional matrix. Where the genomic sequences are from a population of organisms, the method 101 may include depicting at least a portion of the DAG to illustrate genetic diversity within the population. While in the preferred genomic embodiment the DAG is a genomic reference DAG, a DAG according to the invention can represent any nucleotide or amino acid sequence. In certain embodiments, the DAG can represent subsets of a reference genome, such as expressed sequences, repetitive elements, fragile sites, and the like.

FIGS. 2-9 illustrate the use of graph data structures to represent biological sequence data. A graph data structure provides one example of biological information represented using a data structure that may be particular to a location in a computer system. Methods disclosed herein can be used to send that information to a new location at which a structure such as a graph data structure can be re-created so that the information can be accessed, used, or updated in the new location. To illustrate the sending and cloning by serialization and deserialization, the implementation of a genomic DAG and the serialization and deserialization of such a DAG will be described. In some embodiments, a genomic DAG is obtained by first obtaining genomic sequences, which may be obtained as sequence reads, from a database, or both. Sequence reads may be obtained from a sequencing instrument, e.g., by sequencing nucleic acid from a sample.

Figure 2:
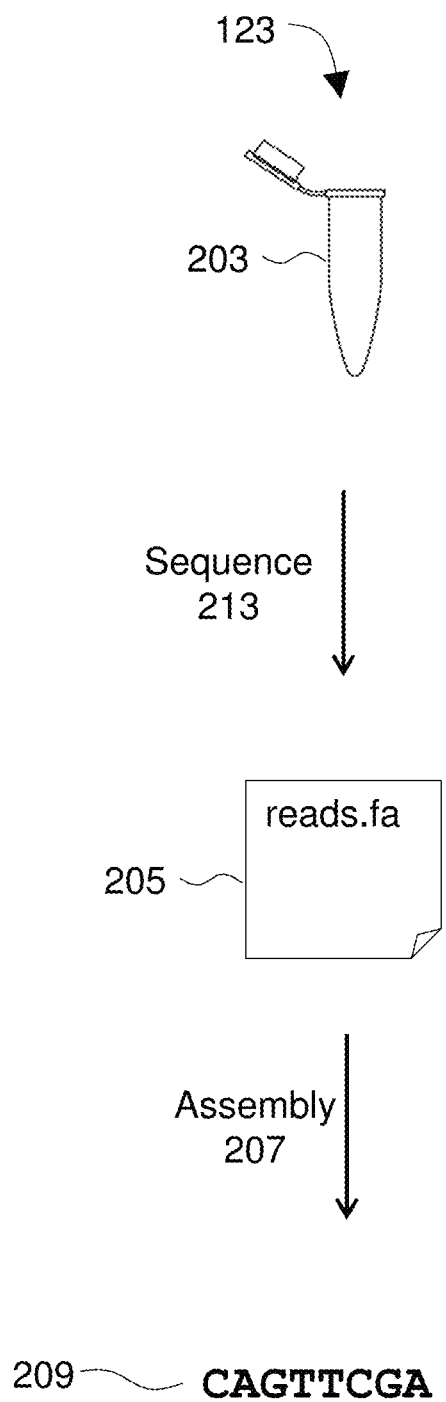
FIG. 2 illustrates obtaining sequence reads from a sample.

FIG. 2 illustrates obtaining 213 sequence reads 205 from a sample 203. As a preliminary step (not depicted), nucleic acid may be isolated or enriched using methods known in the art. In certain embodiments, sequence reads 205 are obtained by performing sequencing 213 on a sample 203 from a subject (however in some embodiments, sequence reads are obtained 213 when a read file is transferred into a system of the invention). Sequencing may be by any method and sequencing instrument known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

Sequencing techniques that can be used include, for example: sequencing-by-synthesis systems and the instruments sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024; 5,674,713; and 5,700,673, each incorporated by reference. Another sequencing technique and instrument that can be used is SOLiD technology by Applied Biosystems from Life Technologies Corporation (Carlsbad, Calif.). Another sequencing technique and instrument that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

As shown in FIG. 2, sequencing 213 generates a plurality of sequence reads 205. Reads according to the invention generally include sequences of nucleotide data anywhere from tens to thousands of bases in length. Reads may be stored in any suitable format such as, for example, FASTA or FASTQ format. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 123 in a format such as FASTA, FASTQ, or similar.

In some embodiments, sequence reads 205 are assembled 207 to provide a contig or consensus sequence 209, which contig or consensus sequence is used in finding alignments to a reference (which reference may be a DAG). Sequence assembly 207 may include any suitable methods known in the art including de novo assembly, reference-guided assembly, others, or combinations thereof. In a preferred embodiment, sequence reads are assembled 207 using graph-based alignment methods. See, e.g., U.S. Pub. 2015/0057946 and U.S. Pub. 2015/0056613, both incorporated by reference. Embodiments of a graph and its use are discussed in greater detail below. The result of assembly 207 is a contig or consensus sequence 209 representing the corresponding portions of nucleic acids present in the sample 203. The contig or consensus sequence 209 or one or more of the sequence reads 205 may then be mapped to a reference to find an alignment with an optimal score. As previously noted, methods of the invention may operate where a genomic reference DAG is used as a reference. A reference DAG can be created by transforming reference sequences into a DAG.

Figure 3:
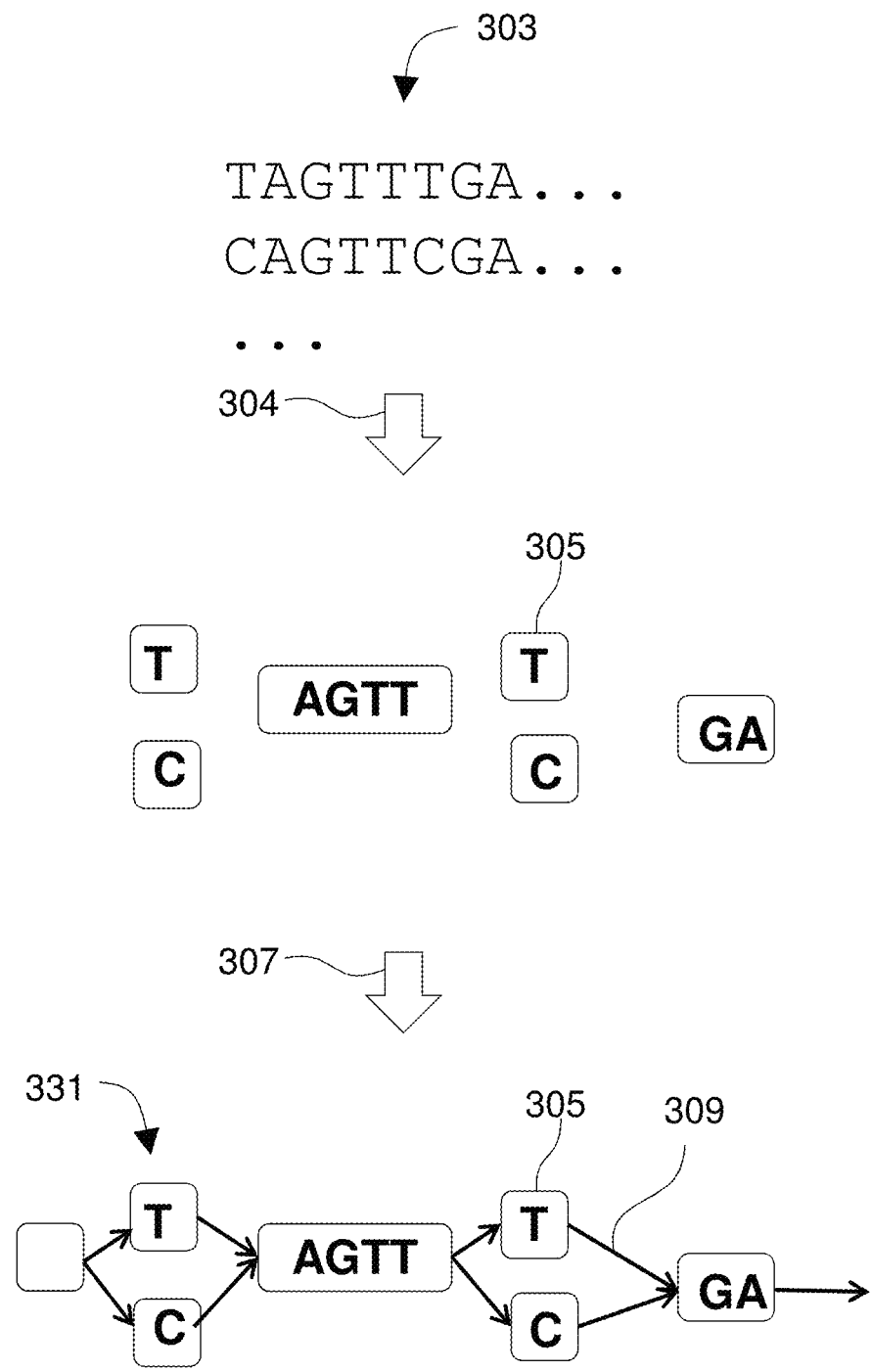
FIG. 3 shows transforming reference sequences into a reference DAG.

FIG. 3 illustrates obtaining reference sequences 303 and transforming 304 the reference sequences 303 into a reference DAG 331 that includes vertex objects 305 and edge objects 309. The reference sequences 303 may be retrieved from a database. For example, a computer system may be used to execute instructions (e.g., using SQL, Perl, Python, or similar suitable scripting and query platform) to retrieve genome sequence data from the NCBI database. From the GenBank database, users can download reference sequences by accession number. By defining a search term based on the accession number and sending it using, e.g., Perl or Python, a local computer can obtain the sequences 303 from an online database.

Each of the sequences 303 are aligned to one another, preferably by being aligned to an object containing information from each other sequence. In a preferred embodiment, the sequences are aligned by the process of building them into the reference DAG using the modified multi-dimensional Smith Waterman operation defined herein. In some embodiments, it may be useful or convenient to perform a multiple sequence alignment among sequences 303, e.g., using Clustal. Multiple sequence alignment is discussed in more detail below. Portions of the sequences that match each other when aligned are identified as blocks and those blocks are transformed 304 into vertex objects 305 that are stored in a tangible memory device.

In the fragments of sequence represented in FIG. 3, it can be seen that bases 2-5 of first sequence align to, and match, bases 2-5 of the second sequence. Thus those segments of those two sequences are identified as a block and systems of the invention create a vertex object 305 to represent that AGTT string. It is noted that this object could potentially be stored using one byte of information. For example, if A=00, C=01, G=10, and T=11, then this block contains 00101111 (one byte). Where the original reference sequences 303 contain thousands of genomes, the described methods provide a considerable improvement to the operation of the computer system in comparison to a prior art method that stores an entire multiple sequence alignment.

The vertex objects 305 are connected 307 to create paths such that there is a path for each of the original sequences. The paths are directed and preferably in the sense that the direction of each path corresponds to the 5' to 3' directionality of the original genomic nucleic acid. The connections creating the paths can themselves be implemented as objects so that the blocks are represented by vertex objects 305 and the connections are represented by edge objects 309. Thus the directed graph comprises vertex and edge objects stored in the tangible memory device. The directed graph or reference DAG 331 represents the plurality of reference sequences 303 in that each one of the original sequences can be retrieved by reading a path in the direction of that path. It is noted that the graph or reference DAG 331 directly depicts branched sequences, thus allowing it to depict homology relationships among the original genomes in a compact form. The graph or reference DAG 331 is a different article than the original sequences 303, at least in that portions of the original sequences that match each other when aligned have been transformed into single vertex objects 305 within branched sequences in the graph or reference DAG 331. Thus if the original article includes 10,000 full genomes in which a segment is perfectly conserved for a span of 1,000 by across all of the genomes, then over 1 million characters of information from the original article, which would require at last 2,000 KB of disk space to store, are transformed into a single object that can use as little as 2 KB on disk. By such means, the known genomes are transformed into a reference DAG. It may be possible to store the sequence strings within either the vertex objects 305 or the edge objects 309 (it should be noted that the terms "node" and "vertex" may be used synonymously). As used herein, node or vertex objects 305 and edge objects 309 refer to objects created using a computer system.

Figure 4:
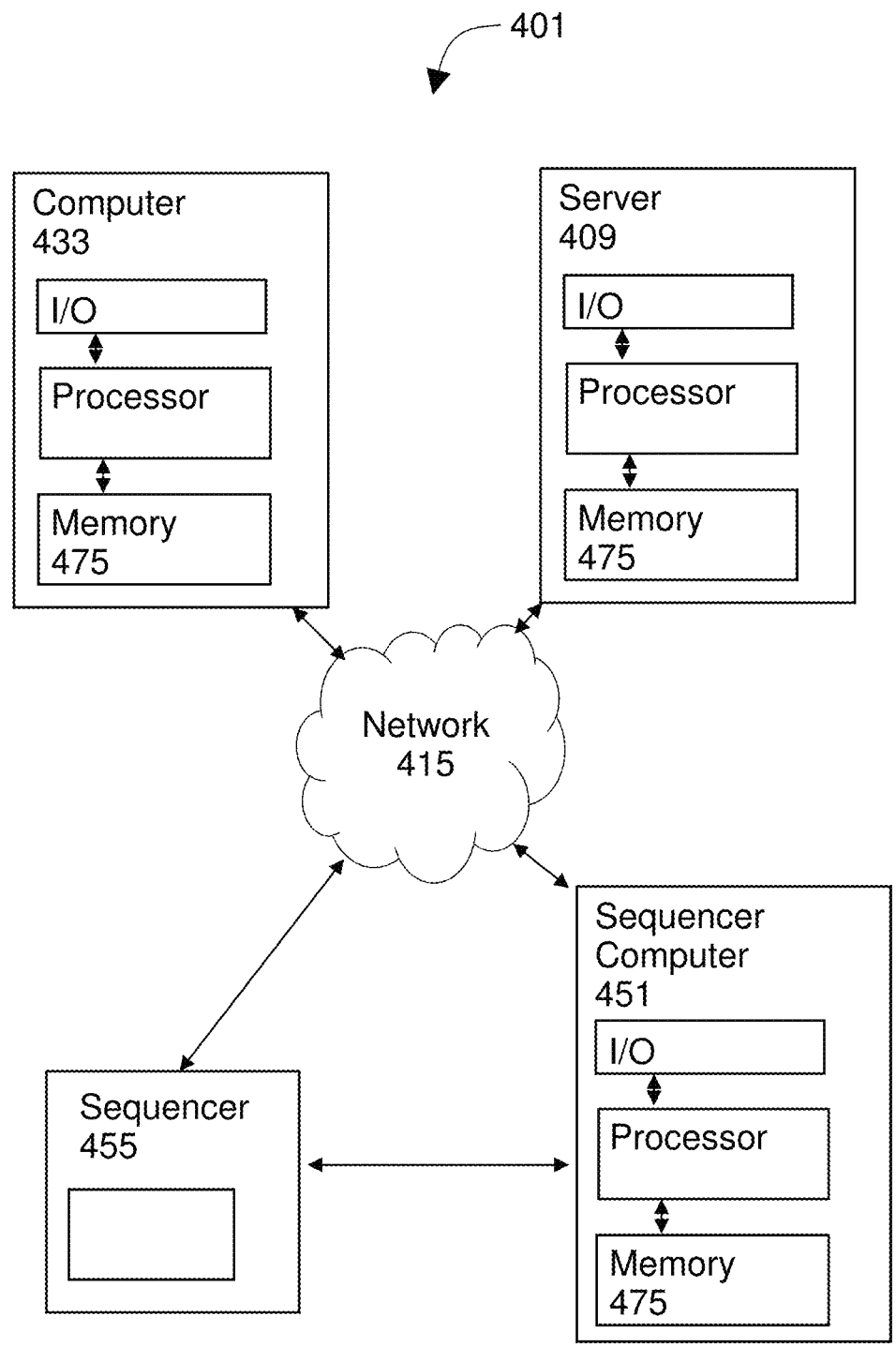
FIG. 4 illustrates a computer system for performing methods of the invention.

FIG. 4 illustrates a computer system 401 suitable for performing methods of the invention. The system 401 includes at least one computer 433. Optionally, the system 401 may further include one or more of a server computer 409 and a sequencer 455, which may be coupled to a sequencer computer 451. Each computer in the system 401 includes a processor coupled to a memory device and at least one input/output device. Thus the system 401 includes at least one processor coupled to a memory subsystem (e.g., a memory device or collection of memory devices 475). Using those mechanical components, the system 401 is operable to obtain a sequence generated by sequencing nucleic acid from a genome of a patient. The system uses the processor to transform the sequence 303 into the reference DAG 331.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The memory subsystem 475 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 401 is operable to store within the memory subsystem 475 a data structure representing biological data (e.g., such as the reference DAG 331 of FIG. 3) and instructions executable by the processor to cause the system to serialize the data structure into a stream of bytes, wherein the stream of bytes can be deserialized into a clone of the data structure that represents the biological data. The system may display biological data from the data structure via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Preferably the reference DAG 331 is stored in the memory subsystem 475 using adjacency lists, adjacency matrices, or index-free adjacency. Those techniques include pointers to identify a physical location in the memory subsystem 475 where each vertex is stored. In a preferred embodiment, the graph is stored in the memory subsystem 475 using adjacency lists. In some embodiments, there is an adjacency list for each vertex. For discussion of implementations see 'Chapter 4, Graphs' at pages 515-693 of Sedgewick and Wayne, 2011, Algorithms, 4th Ed., Pearson Education, Inc., Upper Saddle River N.J., 955 pages, the contents of which are incorporated by reference and within which pages 524-527 illustrate adjacency lists.

Figure 5:
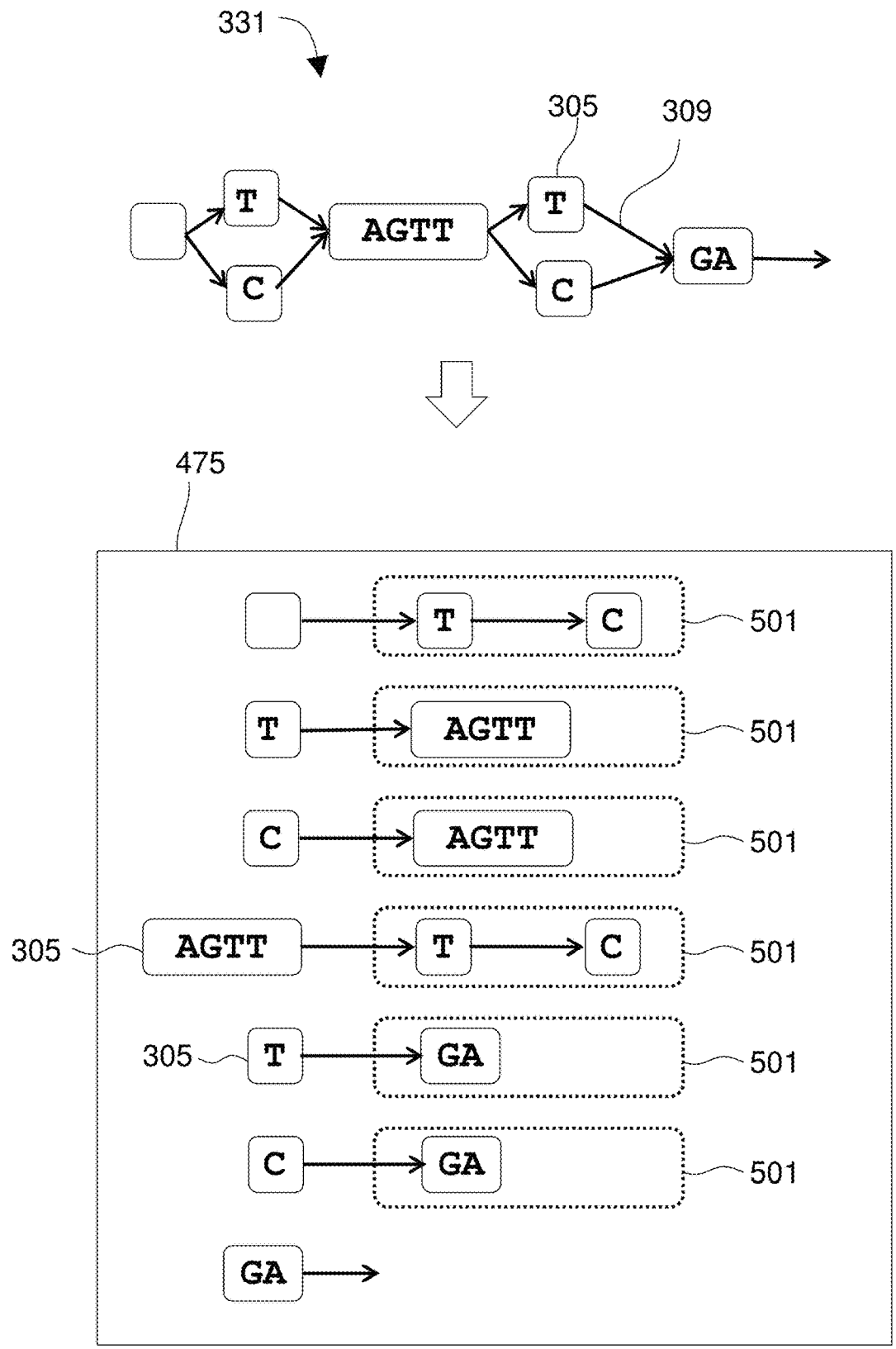
FIG. 5 shows the use of an adjacency list in a genomic DAG.

FIG. 5 shows the use of an adjacency list 501 for each vertex object 305. The system 401 uses a processor to create a graph or reference DAG 331 that includes vertex objects 305 and edge objects 309 through the use of adjacency, i.e., adjacency lists or index free adjacency. Thus, the processor may create the reference DAG 331 using index-free adjacency wherein a vertex object 305 includes a pointer to another vertex object 305 to which it is connected and the pointer identifies a physical location on a memory device 475 where the connected vertex object 305 is stored. The reference DAG 331 may be implemented using adjacency lists such that each vertex object 305 or edge object 309 stores a list of such objects that it is adjacent to. Each adjacency list comprises pointers to specific physical locations within a memory device for the adjacent objects.

In the top part of FIG. 5, the reference DAG 331 is illustrated in a cartoon-like visual-friendly format. The reference DAG 331 will typically be stored on a physical device of memory subsystem 475 in a fashion that provide for very rapid traversals. In that sense, the bottom portion of FIG. 5 is not cartoon-like and represents that objects are stored at specific physical locations on a tangible part of the memory subsystem 475. Each vertex object 305 is stored at a physical location, the location of which is referenced by a pointer in any adjacency list 501 that references that node. Each vertex object 305 has an adjacency list 501 that includes every adjacent node in the reference DAG 331. The entries in the list 501 are pointers to the adjacent nodes. The memory subsystem 475 as shown in FIG. 5 illustrates the need for methods of the invention in that if the adjacency lists 501 were merely copied to a new device (e.g., from within FIG. 4), the pointers would lose meaning, as they point to specific locations within the memory subsystem 475.

In certain embodiments, there is an adjacency list for each vertex and edge and the adjacency list for a vertex or edge lists the edges or vertices to which that vertex or edge is adjacent.

Figure 6:
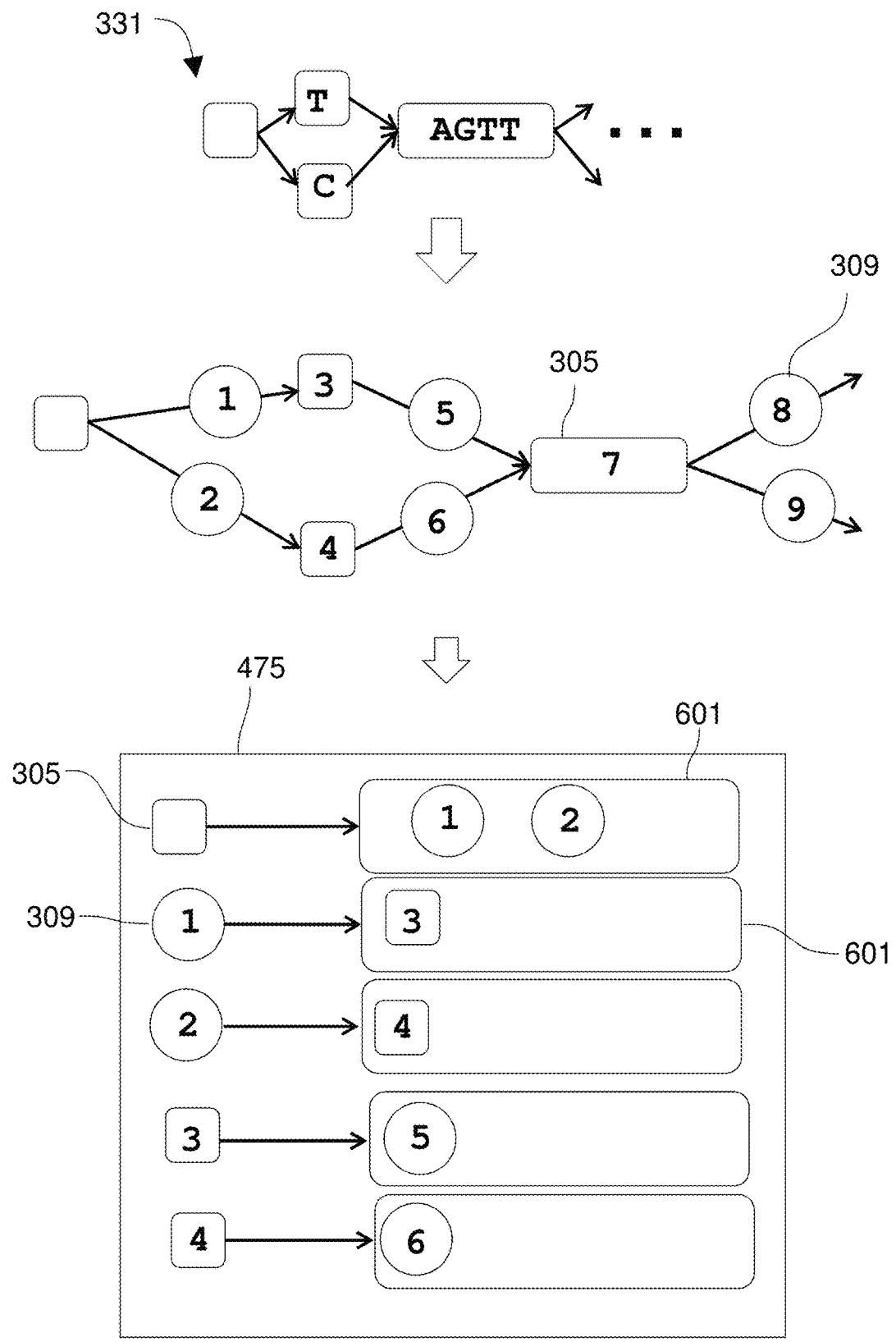
FIG. 6 presents an alternative use of adjacency lists.

FIG. 6 shows the use of an adjacency list 601 for each vertex object 305 and edge object 309. As shown in FIG. 6, system 401 creates the reference DAG 331 using an adjacency list 601 for each vertex and edge, wherein the adjacency list 601 for a vertex object 305 or edge object 309 lists the edges or vertices to which that vertex or edge is adjacent. Each entry in adjacency list 601 is a pointer to the adjacent vertex or edge.

Preferably, each pointer identifies a physical location in the memory subsystem at which the adjacent object is stored. In the preferred embodiments, the pointer or native pointer is manipulatable as a memory address in that it points to a physical location on the memory and permits access to the intended data by means of pointer dereference. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows a sequence to be queried against a large-scale genomic reference graph or reference DAG 331 representing millions or billions of bases, using a computer system 401. Such a graph representation provides means for fast random access, modification, and data retrieval.

Figure 7:
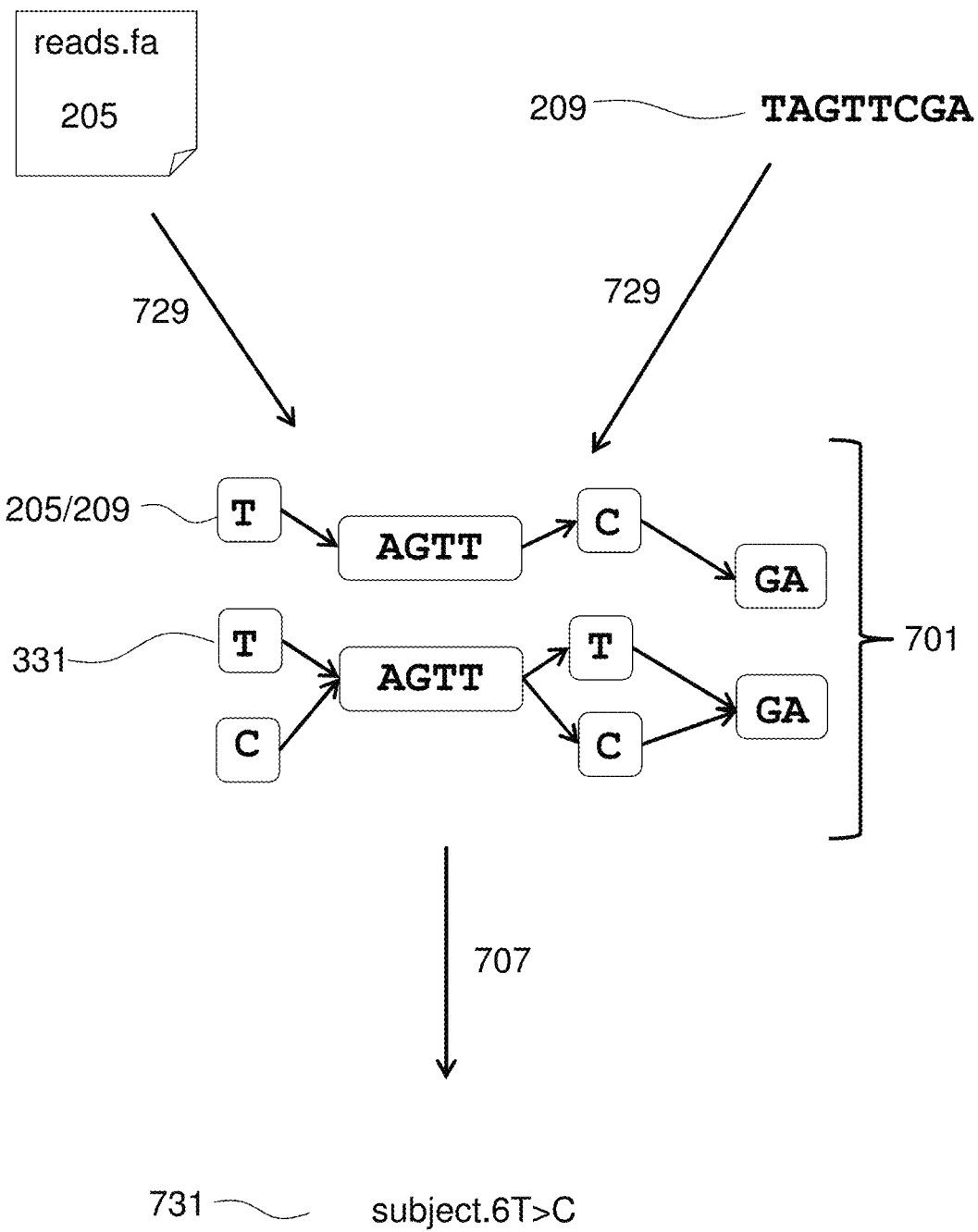
FIG. 7 presents an alignment between a sequence and a reference DAG.
Figure 8:
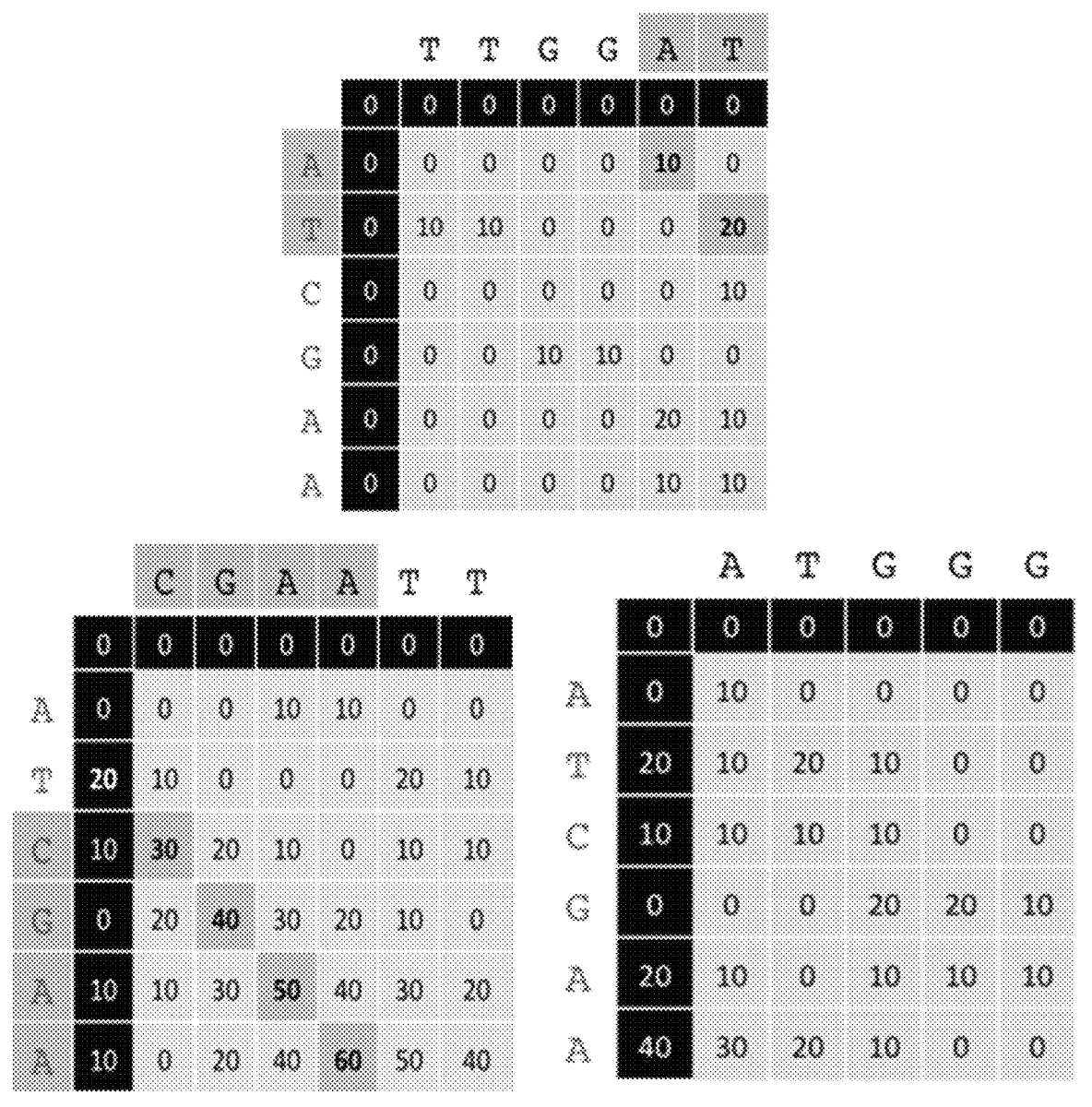

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, each incorporated by reference), which obviates the need for index look-ups, allowing traversals (e.g., as done in the modified SW alignment operation described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described below). Specifically, index-free adjacency can be implemented such that the pointers contained within elements are references to a physical location in memory. FIGS. 7-8 illustrate an applied use of a reference DAG.

FIG. 7 illustrates finding 729 alignments 701 between the sequence reads 205 and the reference DAG 331. In brief, sequence reads 205 are obtained. The reads 205 are aligned 729 to a genomic reference DAG 331. The sequence reads are aligned to the branching sequences of the reference DAG that account for possible genetic variation found in known genomes that are included. The reads may be aligned to the genomic reference DAG using a multi-dimensional modified Smith-Waterman operation described below that provides excellent alignment accuracy and allows for sequence resolution not possible with conventional algorithms. For additional discussion, see U.S. Pub. 2015/0057946, incorporated by reference. The two input paths of FIG. 7 indicate that any suitable input may be used such as reads 205 from a read file or a consensus sequence 209 or any other sequence.

Using alignment operations of the invention, reads can be rapidly mapped to the reference DAG 331 despite their large numbers or short lengths. A modified Smith-Waterman operation for comparing a sequence to a reference graph is provided here as an extension of pairwise alignment methods.

Pairwise alignment generally involves placing one sequence along part of a target, introducing gaps according to an algorithm, scoring how well the two sequences match, and preferably repeating for various positions along the reference. The best-scoring match is deemed to be the alignment and represents an inference of homology between alignment portions of the sequences. A pairwise alignment, generally, involves—for sequence Q (query) having m characters and a reference genome T (target) of n characters—finding and evaluating possible local alignments between Q and T. For any $1 \leq i \leq n$ and $1 \leq j \leq m$, the largest possible alignment score of T[h ... i] and Q[k ... j], where $h \leq i$ and $k \leq j$, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from $O(m^2 n)$ to $O(mn)$ where m and n are the sequence sizes being compared and is more amenable to parallel processing. In the field of bioinformatics, it is Gotoh's modified algorithm that is often referred to as the Smith-Waterman algorithm.

The Smith-Waterman (SW) algorithm aligns linear sequences by rewarding overlap between bases in the sequences, and penalizing gaps between the sequences. SW is expressed for an j×k matrix B, representing the two strings of length j and k, in terms of equation (1).

The optimum alignment can be represented as B[j,k] in equation (1) below:

$$B[j,k] = \max(p[j,k], i[j,k], d[j,k], 0) \text{ (for } 0 < j \leq m, 0 < k \leq n) \quad (1)$$

The arguments of the maximum function, B[j,k], are outlined in equations (2)-(4) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (2), below:

$$p[j,k] = \max(p[j-1,k-1], i[j-1,k-1], d[j-1,k-1]) + \text{MISMATCH\_PEN, if } S[j] \neq A[k] = \max(p[j-1,k-1], i[j-1,k-1], d[j-1,k-1]) + \text{MATCH\_BONUS, if } S[j] = A[k] \quad (2)$$

the insertion argument i[j,k], is given by equation (3), below:

$$i[j,k] = \max(p[j-1,k] + \text{OPENING\_PEN}, i[j-1,k], d[j-1,k] + \text{OPENING\_PEN}) + \text{INSERTION\_PEN} \quad (3)$$

and the deletion argument d[j,k], is given by equation (4), below:

$$d[j,k]=\max(p[j,k-1]+\text{OPENING\_PEN}, i[j,k-1]+\text{OPENING\_PEN}, d[j,k-1])+\text{DELETION\_PEN} \quad (4)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:
 MATCH_BONUS: 10
 MISMATCH_PEN: −20
 INSERTION_PEN: −40
 OPENING_PEN: −10
 DELETION_PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention use a modified Smith-Waterman operation that involves a multi-dimensional look-back through the reference DAG 331. Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the graph-type reference. That alignment algorithm identifies the maximum value for Ci,j by identifying the maximum score with respect to each sequence contained at a position on the graph. In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic graph system that employs physical memory addressing (e.g., through the use of native pointers or index free adjacency as discussed above). The combination of multi-dimensional alignment to a graph or reference DAG 331 with the use of spatial memory addresses (e.g., native pointers or index-free adjacency) improves what the computer system is capable of, facilitating whole genomic scale analysis to be performed using the methods described herein.

The operation includes aligning a sequence, or string, to a graph. For the purpose of defining the operation, let S be the string being aligned, and let D be the directed graph to which S is being aligned. The elements of the string, S, are bracketed with indices beginning at 1. Thus, if S is the string ATCGAA, S[1]=A, S[4]=G, etc.

In certain embodiments, for the graph, each letter of the sequence of a node will be represented as a separate element, d. In a preferred embodiment, node or edge objects contain the sequences and the sequences are stored as the longest-possible string in each object. A predecessor of d is defined as:

(i) If d is not the first letter of the sequence of its object, the letter preceding d in its object is its (only) predecessor;

(ii) If d is the first letter of the sequence of its object, the last letter of the sequence of any object that is a parent of d's object is a predecessor of d.

The set of all predecessors is, in turn, represented as P[d].

In order to find the "best" alignment, the algorithm seeks the value of M[j,d], the score of the optimal alignment of the first j elements of S with the portion of the graph preceding (and including) d. This step is similar to finding Hi,j in equation 1 above. Specifically, determining M[j,d] involves finding the maximum of a, i, e, and 0, as defined below:

$$M[j,d]=\max\{a,i,e,0\} \quad (5)$$

where $$e=\max\{M[j,p^*]+\text{DELETE\_PEN}\} \text{ for } p^* \text{ in } P[d]$$

$$i=M[j-1,d]+\text{INSERT\_PEN}$$

$$a=\max\{M[j-1,p^*]+\text{MATCH\_SCORE}\} \text{ for } p^* \text{ in } P[d], \text{ if } S[j]=d;$$

$$\max\{M[j-1,p^*]+\text{MISMATCH\_PEN}\} \text{ for } p^* \text{ in } P[d], \text{ if } S[j]\neq d$$

As described above, e is the highest of the alignments of the first j characters of S with the portions of the graph up to, but not including, d, plus an additional DELETE_PEN. Accordingly, if d is not the first letter of the sequence of the object, then there is only one predecessor, p, and the alignment score of the first j characters of S with the graph (up-to-and-including p) is equivalent to M[p]+DELETE_PEN. In the instance where d is the first letter of the sequence of its object, there can be multiple possible predecessors, and because the DELETE_PEN is constant, maximizing [M[p*]+DELETE_PEN] is the same as choosing the predecessor with the highest alignment score with the first j characters of S.

In equation (5), i is the alignment of the first j−1 characters of the string S with the graph up-to-and-including d, plus an INSERT_PEN, which is similar to the definition of the insertion argument in SW (see equation 1).

Additionally, a is the highest of the alignments of the first j characters of S with the portions of the graph up to, but not including d, plus either a MATCH_SCORE (if the jth character of S is the same as the character d) or a MISMATCH_PEN (if the jth character of S is not the same as the character d). As with e, this means that if d is not the first letter of the sequence of its object, then there is only one predecessor, i.e., p. That means a is the alignment score of the first j−1 characters of S with the graph (up-to-and-including p), i.e., M[j−1,p], with either a MISMATCH_PEN or MATCH_SCORE added, depending upon whether d and the jth character of S match. In the instance where d is the first letter of the sequence of its object, there can be multiple possible predecessors. In this case, maximizing {M[j, p*]+MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for a sequence reads 205 to the reference DAG 331 by calculating not only the insertion, deletion, and match scores for that element, but looking backward (against the direction of the graph) to any prior nodes on the graph to find a maximum score.

It is worth noting briefly in connection with FIG. 7 that aligning reads to a reference lies at the core of variant calling and variant calling with a genomic reference DAG 331 is included in the scope of the invention. Thus in some embodiments, methods of the invention may be used for variant calling 707 to produce genotype information 731 such as variant calls. The variant calling can include aligning sequence reads to the graph and reporting SNP alleles in a format such as a Sequence Alignment Map (SAM) or a Variant Call Format (VCF) file. Some background may be found in Li & Durbin, 2009, Fast and accurate short read alignment with Burrows-Wheeler Transform. Bioinformatics 25:1754-60 and McKenna et al., 2010, The Genome Analysis Toolkit: a MapReduce framework for analyzing next-generation DNA sequencing data, Genome Res 20(9): 1297-1303, the contents of each of which are incorporated by reference. Variant calling 731 produces results ("variant calls") that may be stored as a sequence alignment map (SAM) or binary alignment map (BAM) file—comprising an alignment string (the SAM format is described, e.g., in Li, et al., The Sequence Alignment/Map format and SAMtools, Bioinformatics, 2009, 25(16):2078-9). Additionally or alternatively, output from the variant calling may be provided in a variant call format (VCF) file. A typical VCF file will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. Further discussion may be found in U.S. Pub. 2013/0073214; U.S. Pub. 2013/0345066; U.S. Pub. 2013/0311106; U.S. Pub. 2013/0059740; U.S. Pub. 2012/0157322; U.S. Pub. 2015/0057946 and U.S. Pub. 2015/0056613, each incorporated by reference.

FIG. 8 shows the matrices that represent the comparison. The modified Smith-Waterman operation of the invention identifies the highest score and performs a backtrack to identify the proper alignment of the sequence. See, e.g., U.S. Pub. 2015/0057946 and U.S. Pub. 2015/0056613, both incorporated by reference. Systems and methods of the invention can be used to provide a report that identifies a modified base at the position within the genome of the subject. Other information may be found in Kehr et al., 2014, Genome alignment with graph data structures: a comparison, BMC Bioinformatics 15:99 and Lee, 2003, Generating consensus sequences from partial order multiple sequence alignment graphs, Bioinformatics 19(8):999-1008, both incorporated by reference.

While genomic reference DAG embodiment and its use depicted in FIGS. 2-7 are not the only applicable data structure for methods of the invention, methods of the invention are particularly well-suited for graph genome applications. In certain embodiments, methods of the invention are provided for Graph Genome Compression and Serialization (GGCS). The GGCS may include containerization of data. Using a containerization schema of the invention, data are represented by a sequence of containers. Preferably, the containers are intrinsically linear in that a container defines a sequence of regions each of which contains a sequence or string of data.

Any suitable containerization scheme may be employed. In some embodiments, each container is a sequence that includes five regions: an opening tag; a size; a type; data; and a closing tag.

Figure 9:
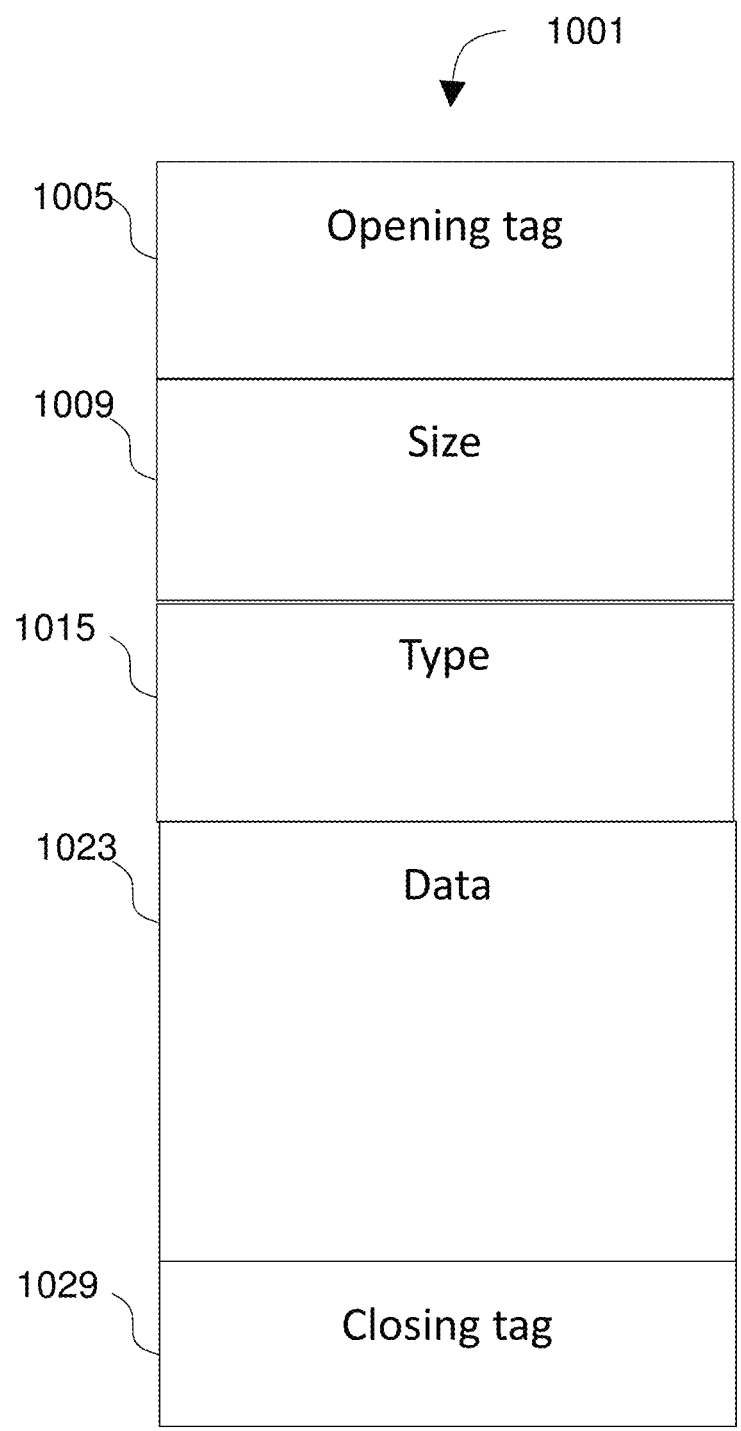
FIG. 9 illustrates a container schema.

FIG. 9 shows an embodiment of a container 1001 with five regions that includes an opening tag 1005, a size region 1009, a type region 1015, a data region 1023, and a closing tag 1029. The opening tag could be any agreed-upon sequence that marks the beginning of a container. The size region 1009 contains the actual size of the container (not, for example, the maximum size permitted for a container of that type). The type region 1015 indicates the type of data held in the container (for examples, see the description container, producer information container, graph geometry information container, graph content container, graph metadata container, genome mapping container, and custom field container all discussed below). The data region 1023 contains the data of the type indicated in the type region. The closing tag 1029 could be any agreed-upon sequence that marks the closing of the container. Containers 1001 may be implemented in any suitable format. In some embodiments, containers 1001 are created in extensible markup language (XML). Important features of this containerization scheme include its recursive potential; polymorphism, or the ability to generate sub-schemas; as well as linearity and compression friendliness, as explained below.

A containerization scheme according to the invention has recursive potential. For example, containers can contain other containers in the data region 1023, so container-types can be more complex. For example, the data region 1023 of any one container 1001 may include one or multiple other containers.

A containerization scheme according to embodiments of the invention has the ability to generate sub-schemas. Rules can be created or added further constraining the number, type, and order of containers, which can be useful in a given domain. GGCS1, described below, is one such sub-schema.

A containerization scheme according to the invention has linearity and compression-friendliness: containers are intrinsically linear, and they contain sufficient information about their own sizes and data to facilitate compression and transmission.

In one embodiment of a method for the containerization and serialization of graph genomes, dubbed GGCS1, a particular subschema of the containers is employed. The subschema may include the requirement that a container 1001 includes separate but related containers for the geometry and content (i.e., nucleotide sequences) of a graph 331.

Figure 10:
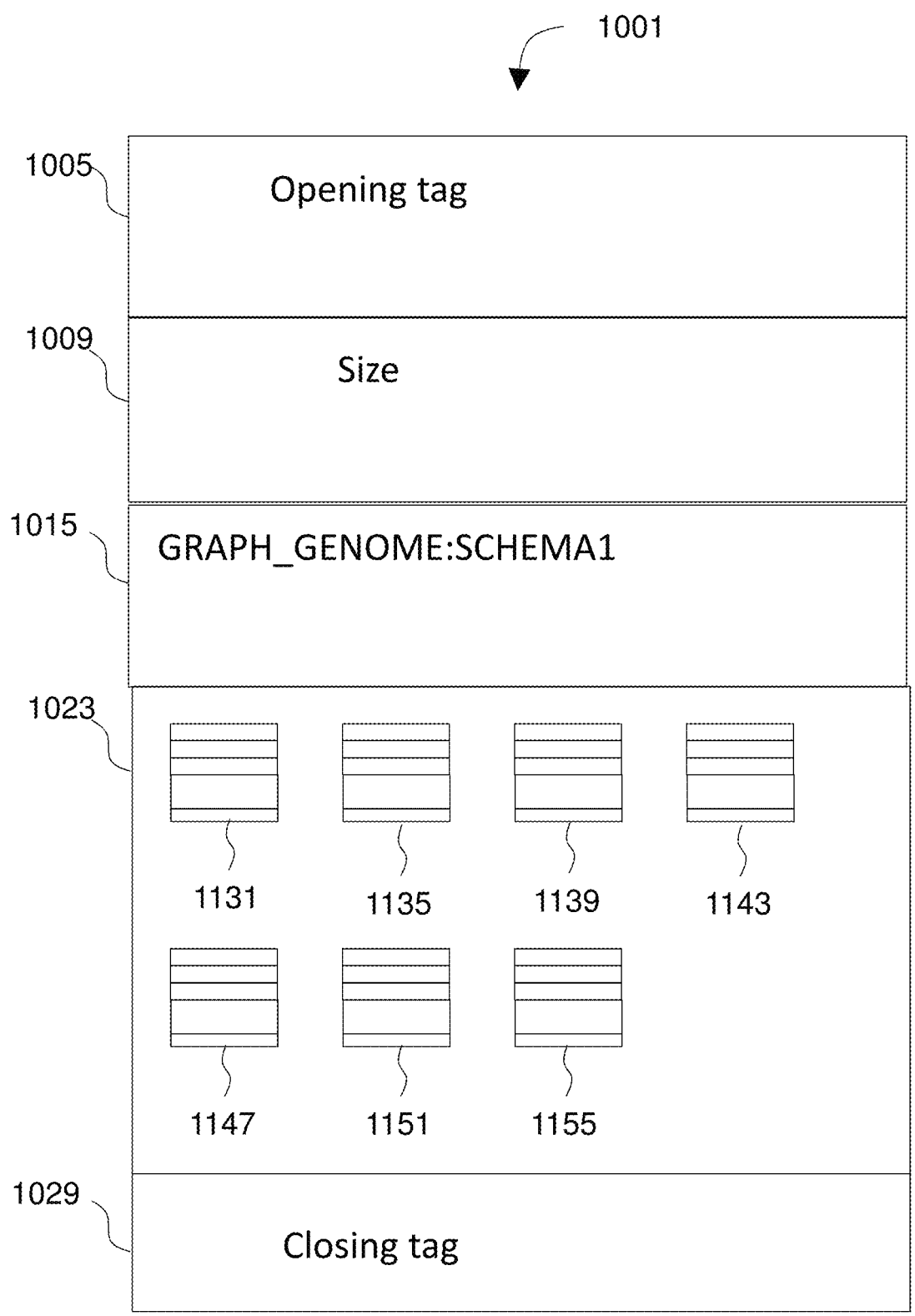
FIG. 10 shows a container according to a certain embodiment.

FIG. 10 illustrates a container 1001 of the GGCS1 embodiment. In the GGCS1 embodiment, a container is created for which the type region is "GRAPH_GENOME: SCHEMA1" and for which the fourth region, the data region 1023, contains seven sub-containers. In the depicted embodiment, of these seven sub-containers, five are optional and two are mandatory. The sub-containers include: a description container 1131, a producer information container 1135, a graph geometry information container 1139, a graph content container 1143, a graph metadata container 1147, a genome mapping container 1151, and a custom field container 1155. The description container 1131 includes a type region that reads "DESCRIPTION:UTF-8," and a data region that contains a description. The producer information container 1135 has a type region 1015 that reads "PRODUCER_INFORMATION:UTF-8," and a data region 1023 that contains information about its producer. The graph geometry information container 1139 and the graph content container 1143 are discussed below in connection with FIG.

11. The graph metadata container 1147 has a type region 1015 that reads "GENOME_GRAPH_METADATA" and a data region 1023 that contains graph metadata. The genome mapping container 1151 has a type region 1015 that reads "GENOME_MAPPING" and a data region 1023 that contains information that is useful for defining and manipulating chromosomes, genes, etc. in a graph context. Finally, the custom field container 1155 can be used for a customized payload ID and custom data.

Figure 11:
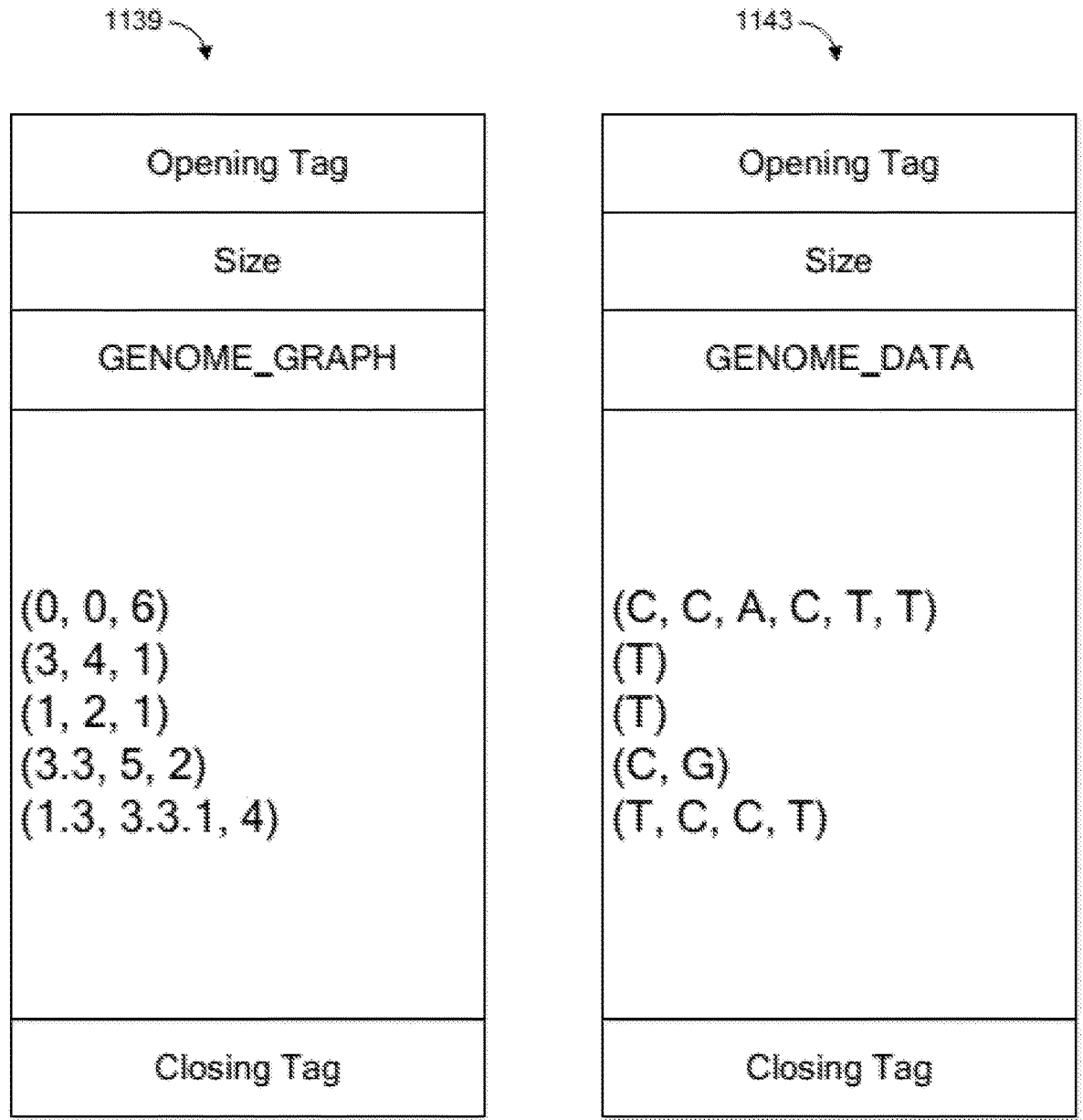
FIG. 11 depicts containers for graph geometry information and content.

FIG. 11 depicts the graph geometry information container 1139 and the graph content container 1143 of FIG. 10 in more detail. The primary information of the genomic reference DAG 331 is serialized into the graph geometry information container 1139 and the graph content container 1143. The (mandatory) graph geometry information container 1139 has a type region 1015 that reads "GENOME_GRAPH" and a data region 1023 that contains information about the geometry of the graph. Besides the geometrical information itself, it can also contain sub-regions for a header and for a list of random access entry points, which can be useful for compression. The (mandatory) graph content container 1143 has a type region reads "GENOME_DATA." Its fourth (data) region contains information about the content of the graph: that is, it contains information sufficient to reconstruct a graph if one already knows the graph's geometry. Besides this information, it also contains sub-regions for a header and for a list of random access entry points, which is useful for compression.

The graph geometry information container 1139 and the graph content container 1143 include important elements of the serialization and deserialization process. Together, they provide a system that serializes graphs by separating a graph's geometry from its content. First, a graph's geometry is expressed as a list of modifications of a basic linear graph. After this list is created, it may be expressed serially. Second, a system is devised for assigning a list of pieces of information to nodes in a graph. Once this assignment system is in place, if one knows the geometry of the graph and the list of pieces of information, one can assign the information to nodes in the graph.

Further, while the graph geometry information container 1139 and graph content 1143 are considered mandatory for the GGCS1 embodiment, in various embodiments, these containers may not necessarily be mandatory. For example, in certain embodiments, graph geometry and content may be stored within a single container. In other embodiments, graph geometry and content may be stored across several containers. Various embodiments are considered to be within the scope of the invention.

An important strength of systems and methods of the invention is that they are agnostic with respect to the biological correlates of the pieces of information (whether or not, for example, they correspond to single nucleotides); with respect to the specifics of the scheme for translating a graph into a system of modifications from a basic linear graph; and with respect to whether the graph representation is or vertex-based.

Figure 12:
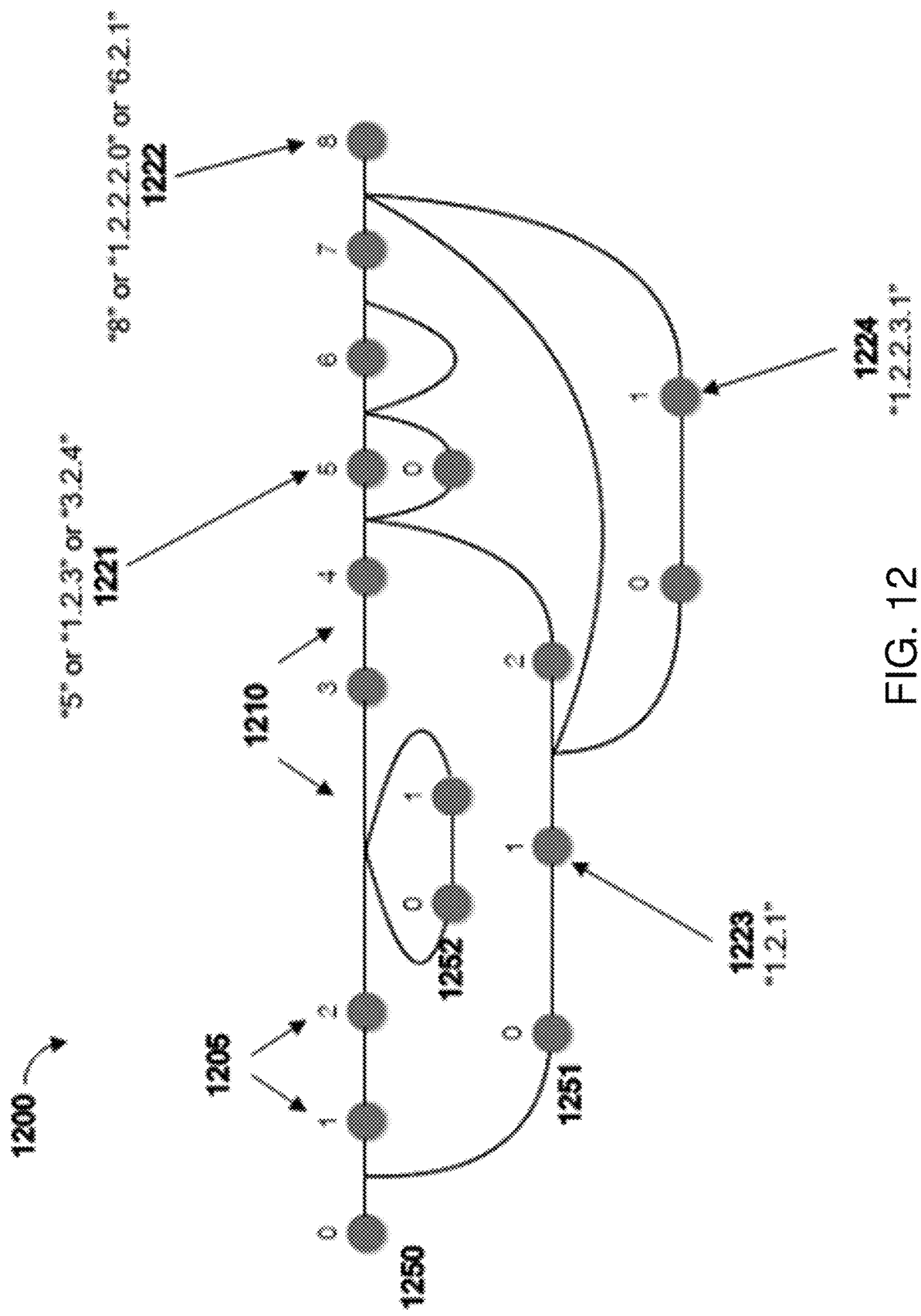
FIG. 12 shows a graph and an exemplary coordinate system for identifying locations within the graph.

A coordinate system may be required to identify particular locations within a graph. As graphs are multidimensional structures, the coordinate system may not be linear. FIG. 12 depicts an exemplary embodiment of a graph 1200. As shown in this embodiment, the graph 1200 comprises a plurality of vertices 1210 (represented by lines) connecting a plurality of edges 1205 (represented by circles). In this embodiment, information (such as nucleotide and protein sequence data) is stored in the edges 1205, which are connected to one another to form paths defined by the vertices 1210. However, in certain embodiments, information may instead be stored in the vertices 1210. It should be noted that the representation of edges as circles and vertices as lines is merely one way of illustrating the graph, chosen because information is stored in the edges in this embodiment; it would be equally valid to represent vertices by circles and edges by lines (e.g., as shown in the embodiment of FIG. 3). The plurality of edges 1205 further comprises edges 1221, 1222, 1223, and 1224, which include exemplary coordinates indicating their location within the graph. Further, it should be noted that while a particular coordinate system is provided, other embodiments may use other coordinate systems.

To assign coordinates and subsequently identify positions within the graph 1200, a set of vertices 1210 connected linearly by a set of edges 1205 can be assigned to a first branch 1250. Each edge 1205 in the first branch 1250 is then assigned a position identifier relative to the first edge 1205 of the branch, i.e., 0, 1, 2, 3, etc. In other words, each position identifier reflects how many vertices must be traversed to arrive at that edge 1205. As shown, the first branch 1250 comprises nine edges 1205 and eight vertices 1210. Accordingly, the last edge 1205 is assigned a position identifier "8" as eight vertices must be traversed to reach that edge.

The remaining edges 1205 and vertices 1210 may then be assigned to additional branches. A second branch 1251 has three edges 1205 and four vertices 1210. The first vertex of the second branch 1251 is connected to the first vertex of the first branch 1250, and the last edge is connected to the fifth edge of the first branch 1250. Similar to the first branch 1250, each vertex in the second branch 1250 is assigned a position identifier indicating the number of edge traversals required to reach that vertex relative to the first vertex in the branch. The remaining vertices and edges may subsequently be assigned to additional branches and assigned positions accordingly.

In certain embodiments, the graph 1200 can be a directed graph, such that the orientation of the edges has a meaning. For example, if the directed graph represents a sequence of nucleotides, an orientation may correspond to the directionality of DNA, i.e., from the 5' to 3' direction. Similarly, if the directed graph represents a protein sequence, the orientations may correspond to the sequential order of amino acids. Starting from the left-most edge of branch 1250, particular locations within the graph 1200 may be identified by specifying the number of vertex traversals and whether any divergent paths are taken. For example, the edge 1221 can be identified by the coordinates "5", indicating a linear traversal of 5 vertices along the first branch 1250. Similarly, the edge 1222 can be identified by the coordinates "8", indicating a traversal of eight vertices from the starting edge at position 0.

Edges may also be identified by following divergent paths at vertices. For example, the edge 1223 may be identified by traversing a single edge to arrive at a first vertex (1), taking the second path from the first vertex (2), and then traversing an additional vertex (1) to arrive at edge 1223. Thus, the edge 1223 can be represented by the coordinates "1.2.1". Edge 1224 can be represented by coordinates "1.2.2.3.1", i.e., traverse one edge to arrive at the first vertex (1), take the second path from the first vertex (2), traverse two vertices (2), take the third path (3), and traverse one vertex to arrive at edge 1224 (1).

Further, edges may be represented by multiple different coordinates depending on the path taken to arrive at that edge through the graph 1200. For example, edge 1221 can also be located by following the second branch 1220 instead of entirely traversing the first branch 1215, i.e., by traversing one edge from the first vertex (1), taking the second path from the first vertex (2), and traversing an additional three vertices (3) to arrive at edge 1221 ("1.2.3"). Another path to arrive at edge 1221 can also be defined by traversing three vertices (3), taking the second path (2), and traversing an additional four vertices (4) to arrive at edge 1221 ("3.2.4.") Similarly, edge 1222 can be identified by traversing one vertex from the first edge (1), taking the second path (2), traversing two vertices (2), taking the second path (2), and arriving at edge 1222 (0) ("1.2.2.2.0"). Edge 1222 can also be located by traversing six vertices (6), taking the second path (2), and traversing an additional vertex (1).

The disclosed coordinate system is highly flexible because it is relative. As shown in this embodiment, any location within the graph 1200 can be characterized with respect to any other location. Further, the disclosed coordinate system may be used with various graphs, including both directed and non-directed graphs. However, while in this embodiment this coordinate system is used, various other coordinate systems may be used according to embodiments of the disclosure. For example, in certain embodiments, a linear coordinate system may be substituted.

Figure 13:
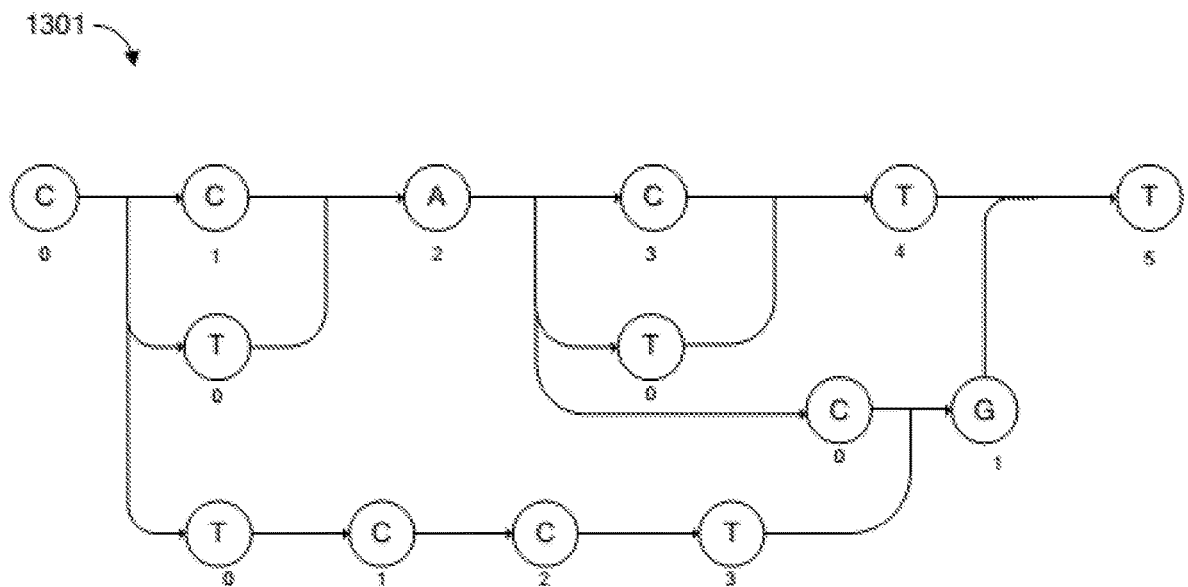
FIG. 13 shows a graph to be serialized and a pair of containers.

FIGS. 13-17 illustrate one embodiment of a method of serialization according to the disclosure. FIG. 13 shows a graph 1301 to be serialized. A coordinate system as described with reference to FIG. 12 is drawn and each edge is assigned a value in relation to its position on a branch. (As previously noted, other coordinate systems are possible and within the scope of the invention.) Given the graph 1301, a routine can be written to serialize the graph. In brief, some arbitrary branch of the path is selected and described by its coordinates and content, and then removed from the graph. The selection, description, and removal is repeated iteratively until the graph topology is linear and no branches remain.

The following pseudocode expresses that iterative operation and can be implemented in any suitable programming language.

(1) Initialize sequences A and B as empty sequences.
(2) While a given graph is not a line:
(2a) Remove a branch from the graph, noting its starting coordinates CS, ending coordinates CE, the number of vertices N on the branch, and the content X_1, X_2, . . . , X_N of those vertices.
(2b) Append a tuple (CS, CE, N) to the front of A.
(2c) Append X_1, X_2, . . . , X_N to the front of B (or append these items to B according to some rule that will complement the traversal rule used in deserialization step (2b) below).

In operation, the serialization method may proceed as illustrated by FIGS. 13-17.

FIG. 13 depicts a graph 1301 labelled according to the coordinate system described above. Additionally, FIG. 13 illustrates two sequences A, B each initialized as empty sequences. Each of the empty sequences may be a container, and thus they may be, respectively, the graph geometry information container 1139 and the graph content container 1143 of FIG. 11.

Figure 14:
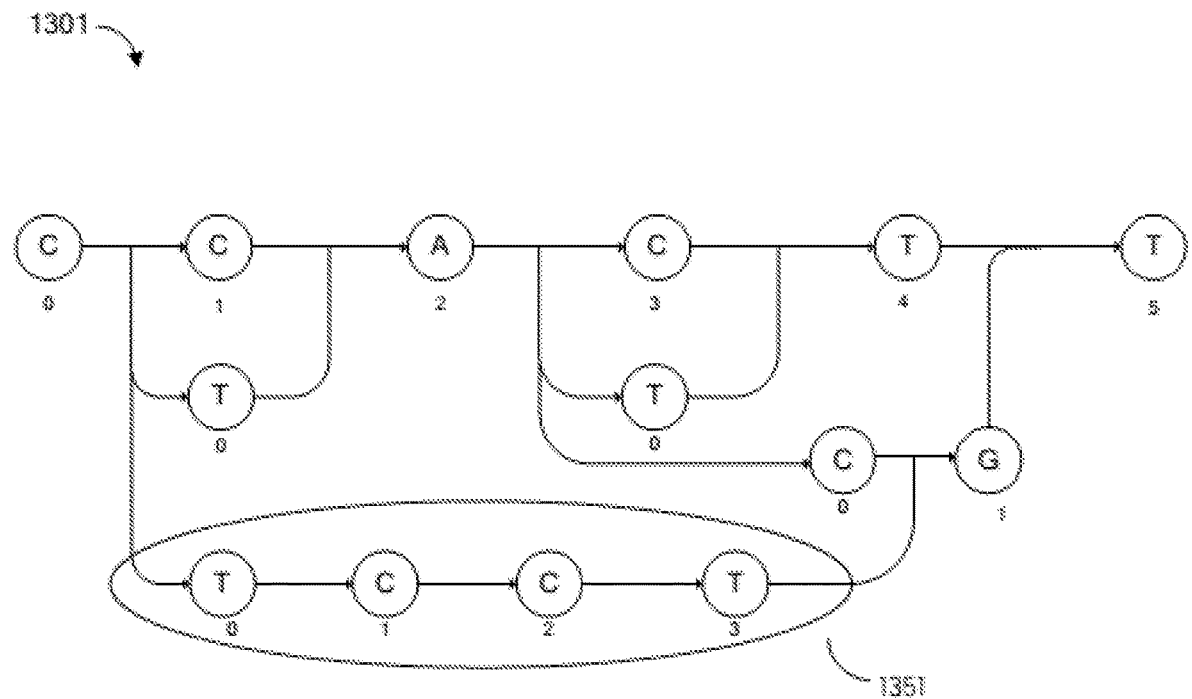
FIG. 14 illustrates a first branch being removed from the graph and the graph data being put into the containers.

FIG. 14 illustrates (while graph 1301 is not a line, i.e., the graph 1301 is not a single linear branch) a branch 1351 selected for removal from the graph. Branch 1351 begins (CS) at coordinates "1.3", indicating that it is located by traversing one edge to arrive at the first vertex and following the third path. Branch 1351 ends (CE) at coordinates "3.3.1", indicating that it joins with the graph at the position located by traversing three vertices, taking the third path, and traversing one vertex. Branch 1351 has 4 (N) vertices, with content X_1, X_2, X_3, X_4 of T, C, C, and T, respectively. Each of these parameters (starting and ending coordinates CS, CE, the number of edges N on the branch, and the content X_1, X_2, . . . , X_N of those edges are all noted.

As shown in the bottom of FIG. 14, a tuple (CS, CE, N) is appended to the front of sequence A. The content X_1, X_2, . . . , X_N is appended to the front of sequence B (or are appended to B according to some rule that will complement the traversal rule used in deserialization step (2b) below). As the geometry and content of branch 1351 have been placed into sequences A and B, the branch 1351 may subsequently be considered to be removed from the graph 1201, as shown in FIG. 15.

Figure 15:
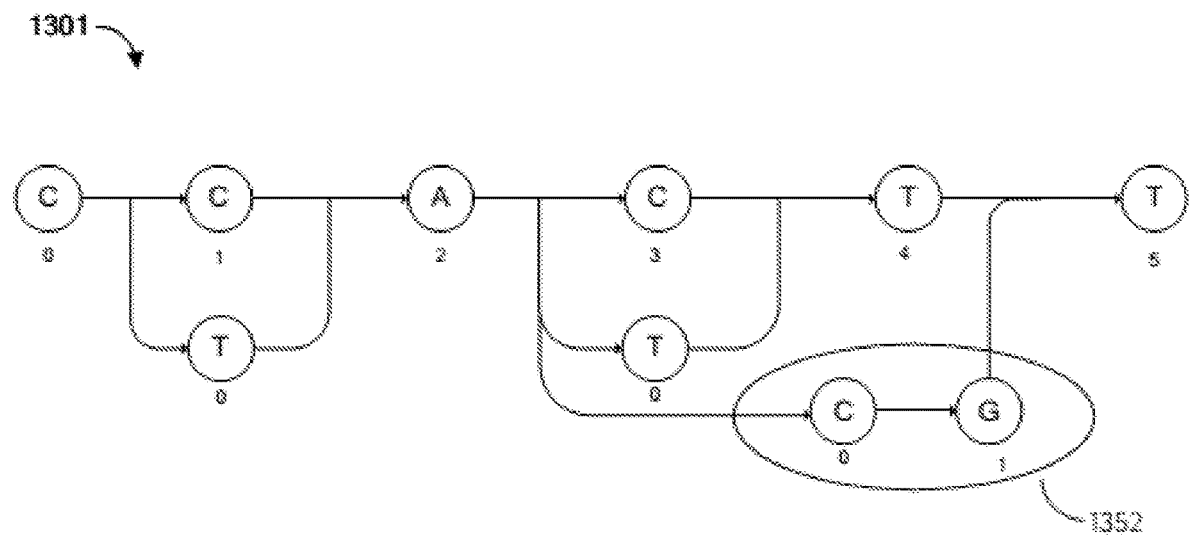
FIG. 15 illustrates a second branch being removed from the graph and the graph data being put into the containers.

FIG. 15 shows the graph 1201 with branch 1351 having been removed and the corresponding data (i.e., the tuple (CS, CE, N) and edge content (X_1, X_2, . . . , X_N) added to sequences A and B. As shown, graph 1201 still contains multiple branches, and is not yet a line. Since graph 1201 is not a line, to continue serialization, another branch will be removed and placed into the sequences A and B. A second branch 1351 is selected for removal. The start (CS) of branch 1352 is located at coordinates "3.3", and end (CE) is located at coordinates "5". The branch 1352 has two edges (N), with content X_1, X_2 of C, G. As shown in the bottom of FIG. 15, this information is appended to the beginning of sequences A and B.

Branch 1352 may then be removed from graph 1301. It should be noted that the branch 1352 need not be literally removed. While it may be literally removed, as the graph 1301 or DAG is pared back, in a preferred embodiment, removal means that the branch 1352 is removed from further consideration for the purposes of the serialization process.

Figure 16:
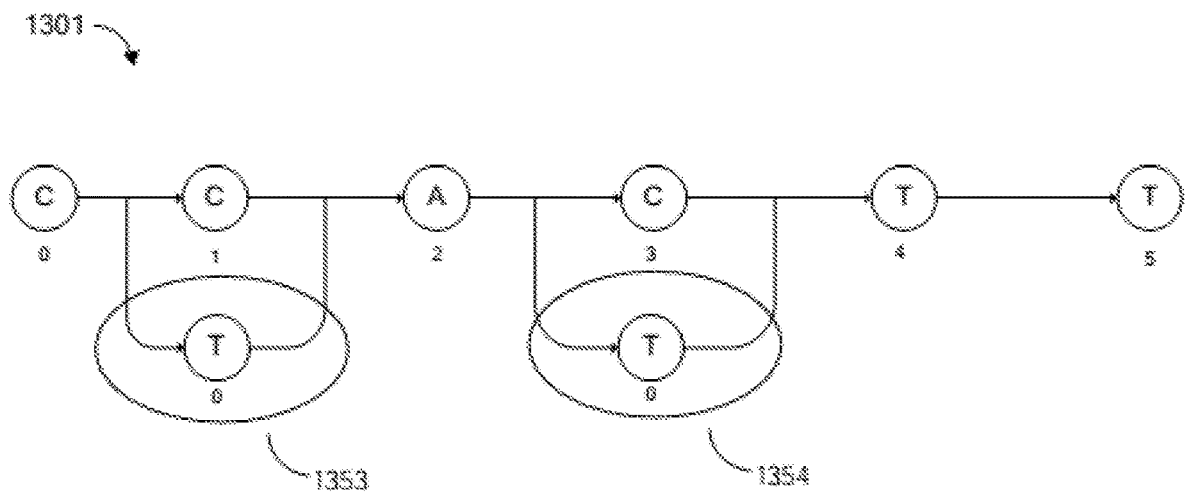
FIG. 16 illustrates third and fourth branches being removed from the graph, with corresponding graph data placed into the containers.

FIG. 16 shows graph 1301 with branch 1352 having been removed. The process will repeat iteratively while graph 1301 is not a line. As shown in this embodiment, two branches 1353, 1354 that will be removed in subsequent iterations are called out in FIG. 16 and their corresponding information is entered into sequences A and B. Branches 1353 and 1354 may then be removed from the graph 1301, as shown in FIG. 17.

Figure 17:
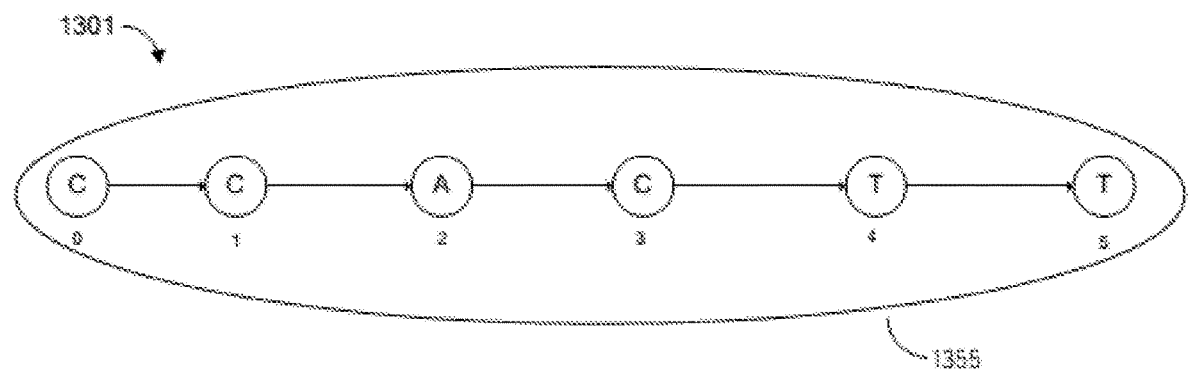
FIG. 17 shows the graph as serialization approaches a final step.

As shown in FIG. 17, the graph 1201 has been reduced to a single line or branch 1355. For a final step of the serialization, the line can be added to the sequences A and B as a branch from graph 1301, leaving nothing left of graph 1301 (remembering that the serialization process need not actually remove the original instance of the graph from the disk). Because the branch is the last remaining branch, it does not have any start or end coordinates, and thus the only parameters stored are a null parameter (such as starting and ending coordinates of 0), the number of vertices N, and the content X_1, X_2, X_3, X_4, X_5, X_6.

The described operation above provides lists of statements A and B which may then be used, respectively, as the graph geometry information container 1139 and the graph content container 1143 within a container 1001 of the GGCS1 embodiment. The described operation reads the geometry and content from a genomic DAG (such as the reference DAG 331 of FIG. 3) and translates it into an inherently linear structure. The GGCS1 container, which can include the graph geometry information container 1139 and the graph content container 1143, may easily be represented or stored as UTF-8 or such format as can be directly streamed linearly. Objects from the DAG associated with an adjacency list or that use index-free adjacency as well as any pointers that indicate a location of an object in memory are not required or included in the GGCS1 container and are not required for reconstructing a clone of the DAG from the GGCS1 container. The container and any associated (e.g., containing or contained) containers can be streamed as a series of bytes.

The stream of bytes can be read at a new location and deserialized by a process that is complementary to the serialization just described. As shown in this embodiment, the lists of statements A and B can be considered to be instructions to rebuild, or deserialize, the graph 1301. Further, the lists of statements A and B can act as a last-in, first-out (LIFO) queue. As the graph is serialized, statements are appended to the front (i.e., prepended) to the lists A and B. Each corresponding pair of statements in the lists A and B (i.e., the graph geometry and its content) identify a branch that may be iteratively added to rebuild the graph 1301. Accordingly, the graph is rebuilt in the reverse order in which it was serialized.

In the serialization example above, the DAG uses one edge for each nucleotide of sequence data. This can be advantageous in that edges do not need to be split or separated into multiple edges in order to accommodate the addition of new branches. However, in certain embodiments, edges may represent strings or sequences of multiple nucleotides. Putting strings into edges may maximize the benefit of a DAG where very large numbers of sequences are involved that include very little variation. The output of a next-generation sequencer that produces short (e.g., 50-300 bp) sequence reads would be a good example. While an output set may include multiple millions of sequence reads, within which are included millions of identical sequence reads, one of the identical sequence reads can be written to a node that then represents all of the millions of identical sequence reads.

A DAG that creates a node for each nucleotide may be better suited for applications in which there is greater variety, but fewer total sequence inputs. Thus, a multiple genome alignment of a conserved gene from across 100,000 samples may be better represented using an edge for each nucleotide. It is also noted that the two DAG formats just described are not incompatible and can easily be integrated one into the other. In fact, the modified Smith Waterman operation described herein can be used to map a nucleotide-per-node DAG to a string-per-node DAG and integrate the two. Additionally, while in this embodiment the content (i.e., nucleotide data) is stored in the edges, in other embodiments content may be stored in the vertices. Various embodiments are considered to be within the scope of the disclosure.

A process for deserializing a serialized genomic DAG is now described with reference to the following pseudocode.
(1) While sequence A is nonempty:
(1a) Remove the first tuple (CS, CE, N) from the front of A.
(1b) Modify the graph to create a branch with N edges starting at coordinates CS and ending at coordinates CE.
(2) While sequence B is nonempty:
(2a) Remove the first item from the front of sequence B.
(2b) Put that item in the next empty edge on the graph, where next is defined by the appropriate traversal rule.

FIGS. 18-23 depict one way in which the deserialization process could work through an exemplary application of the pseudocode. In particular, FIGS. 18-23 illustrate a graph that may be cloned from an original graph by reading from a graph geometry information container and a graph content container, such as the graph geometry information container 1139 and graph content container 1143 within the container 1001 of the GGCS1 embodiment of FIGS. 10-11. In this example, the information within the containers 1139, 1143 is provided in Table 1.

TABLE 1

| Geometry Container 1139 | Content Container 1143 |
|---|---|
| (0, 0, 3) | (T, G, A) |
| (0.2, 3, 0) | |
| (3, 3, 1) | (C) |
| (0.2, 4, 1) | (T) |

Figure 18:
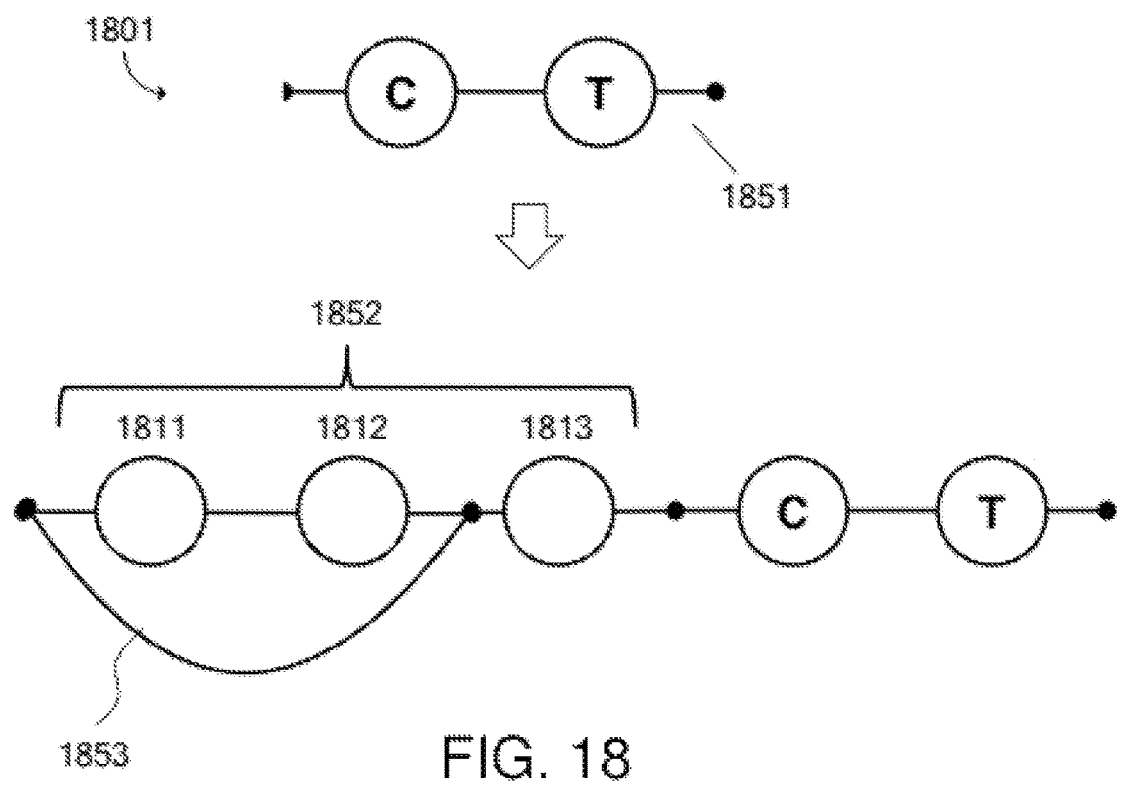
FIG. 18 also shows three edges being added to a graph during deserialization.

As shown in the embodiment of FIG. 18, the graph stored within the containers 1139, 1143 may be appended to a previously existing or instantiated graph, such as the graph 1801 having a single branch 1851. The preexisting graph 1801 has two edges with content C and T, respectively. While in this embodiment, the main branch 1851 is already created, it should be noted that the branch 1851 may also have been serialized and deserialized according to embodiments of the disclosure. For example, the first lines of the containers 1139, 1143 could define this as the last branch of the source graph when the source graph was serialized.

As previously noted, each line in the geometry container 1139 describes a branch to be added to a graph. In this example, the first line of the geometry container 1139 defines a second branch 1852 having three edges 1811, 1812, 1813 that should be appended before the first branch 1851 (start at 0, end at 0, 3 edges). The second line of the geometry container 1139 defines a third branch 1853 having no edges that extends from before the first edge to before the third edge. The third line of the geometry container 1139 defines a fourth branch 1854 with one edge 1814, and the fourth line defines a fifth branch 1855 having one edge 1815.

Figure 19:
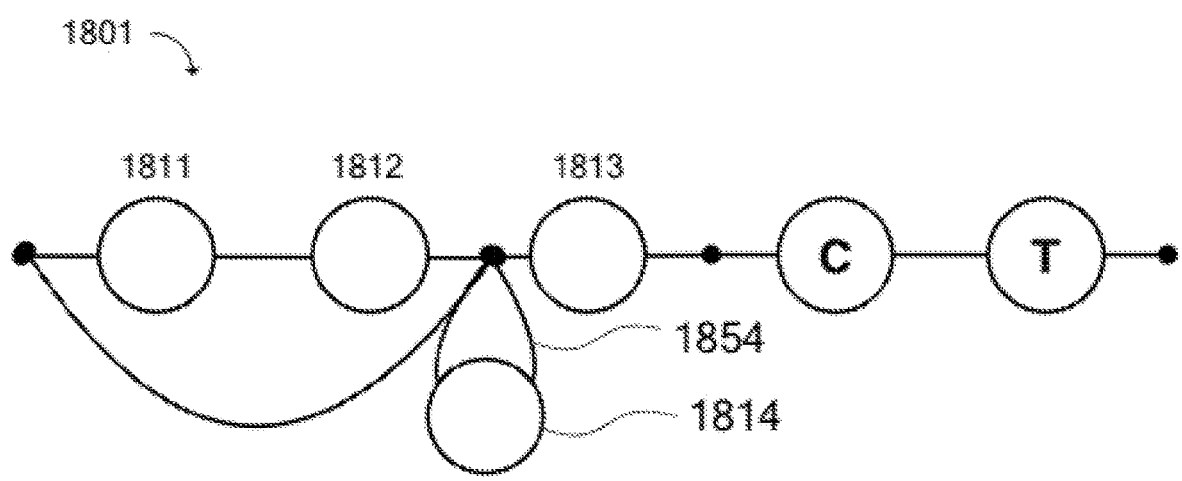
FIG. 19 shows the creation of a branch with one edge.

FIG. 18 illustrates the second and third branches 1852, 1853 added to the graph 1801. The second branch 1852 is positioned or appended before the first branch 1851. It should be noted that while the first and second branches 1851, 1852 are defined separately, they could also be defined together as a single branch. For example, if the graph 1801 is subsequently serialized, branches 1851 and 1852 could be combined into a single entry having 5 edges with corresponding content. Next, the third branch 1853 having no edges is created from before the first edge to before the third edge. FIG. 19 depicts the addition of the fourth branch 1854 with one edge 1854 positioned between the second and third edges 1812, 1813. Continuing to follow the instructions in this fashion, the fourth branch 1854 is added to the graph 1801.

Figure 20:
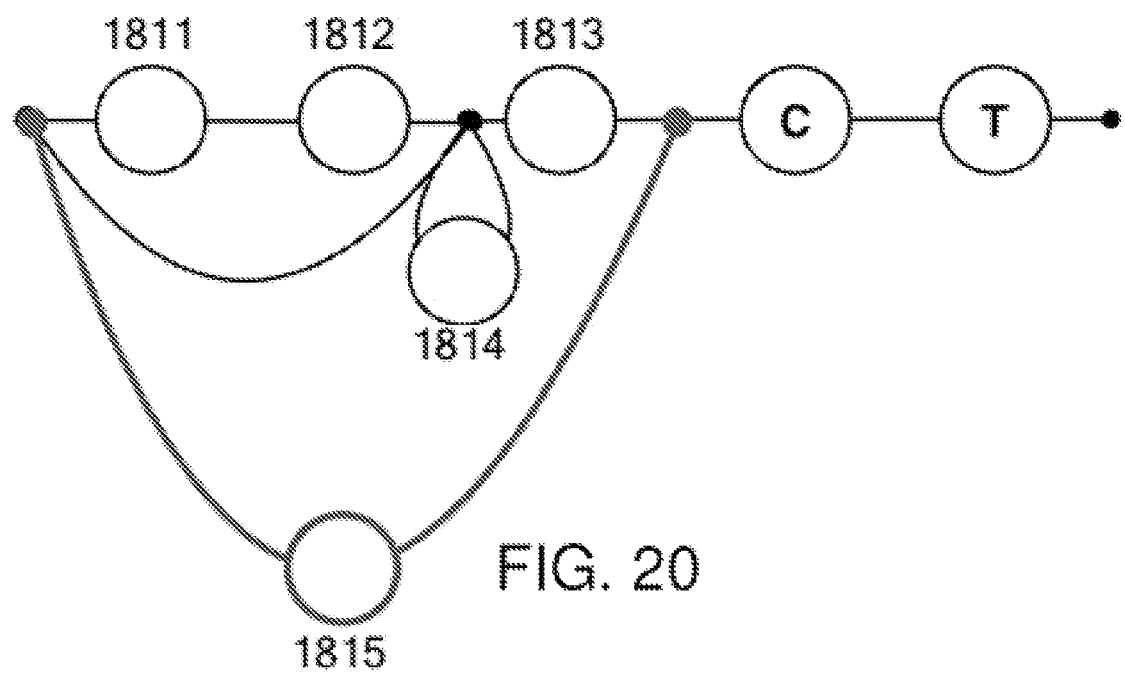
FIG. 20 shows another branch being created.

FIG. 20 illustrates the fifth branch 1855 created from before the first edge 1811 to before the beginning of the main branch to which the graph is appended (after the third edge 1813). In this example, this completes the geometry, or topology, of the graph. Once the topology of the graph is created (or simultaneously therewith), the data or content within the content container 1143 can be populated into the objects or edges. The content is read from the graph content container 1143 where it is stored in a way that corresponds to the steps of the geometry building just described.

Figure 21:
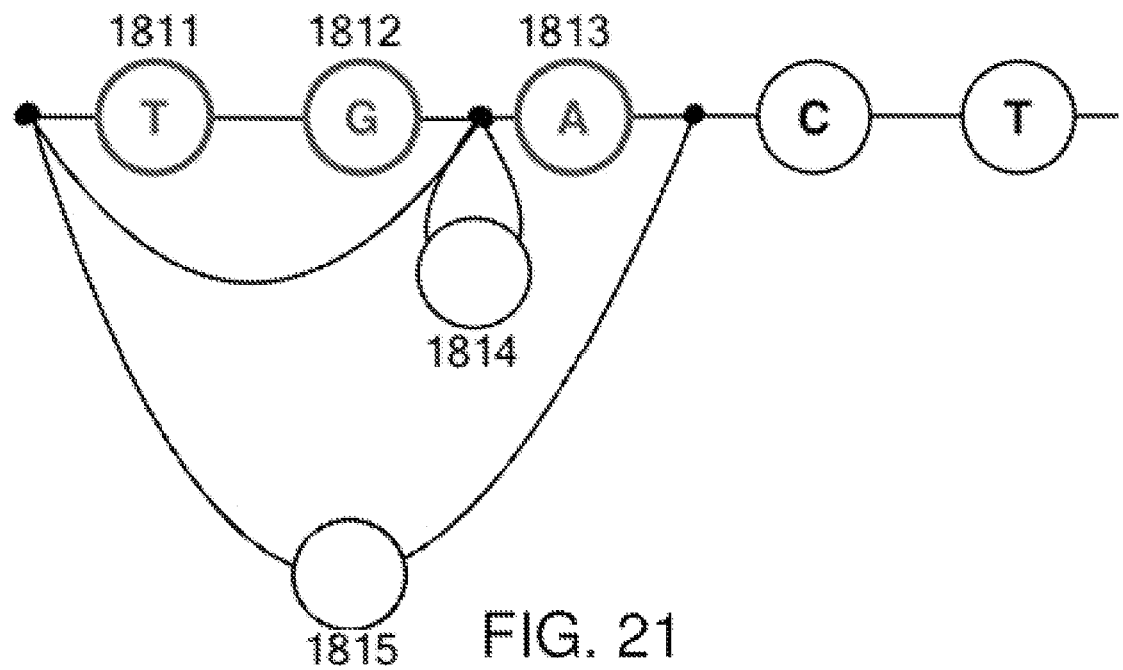
FIG. 21 shows nucleotides being added to edges.
Figure 22:
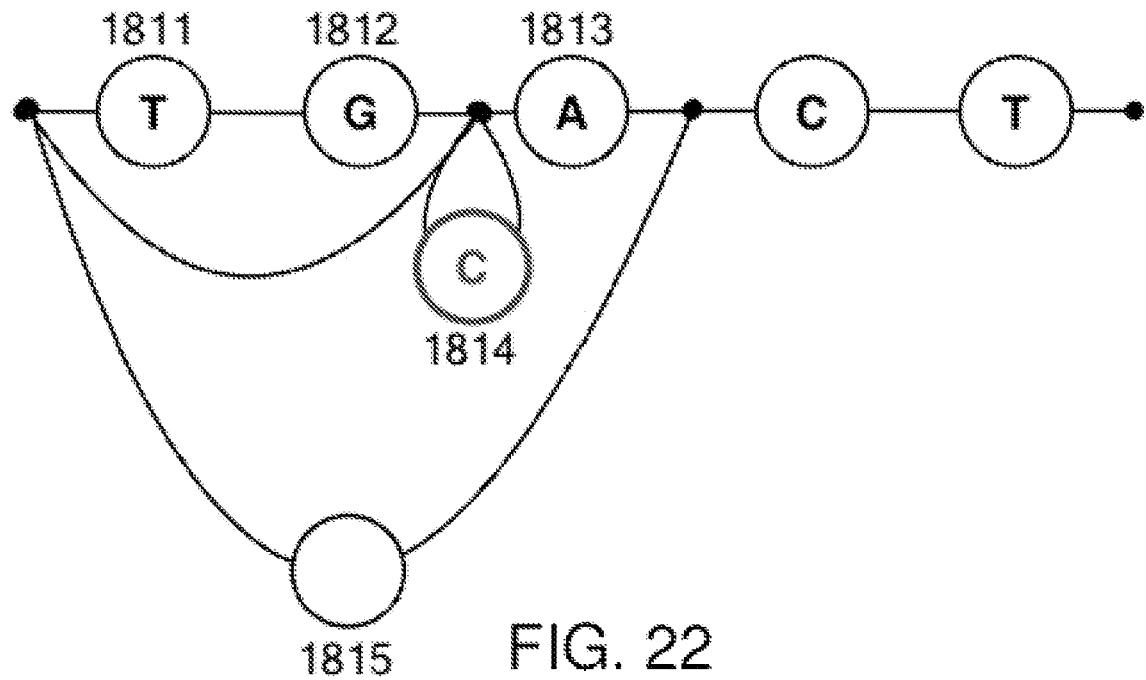
FIG. 22 shows the addition of a nucleotide to an edge.
Figure 23:
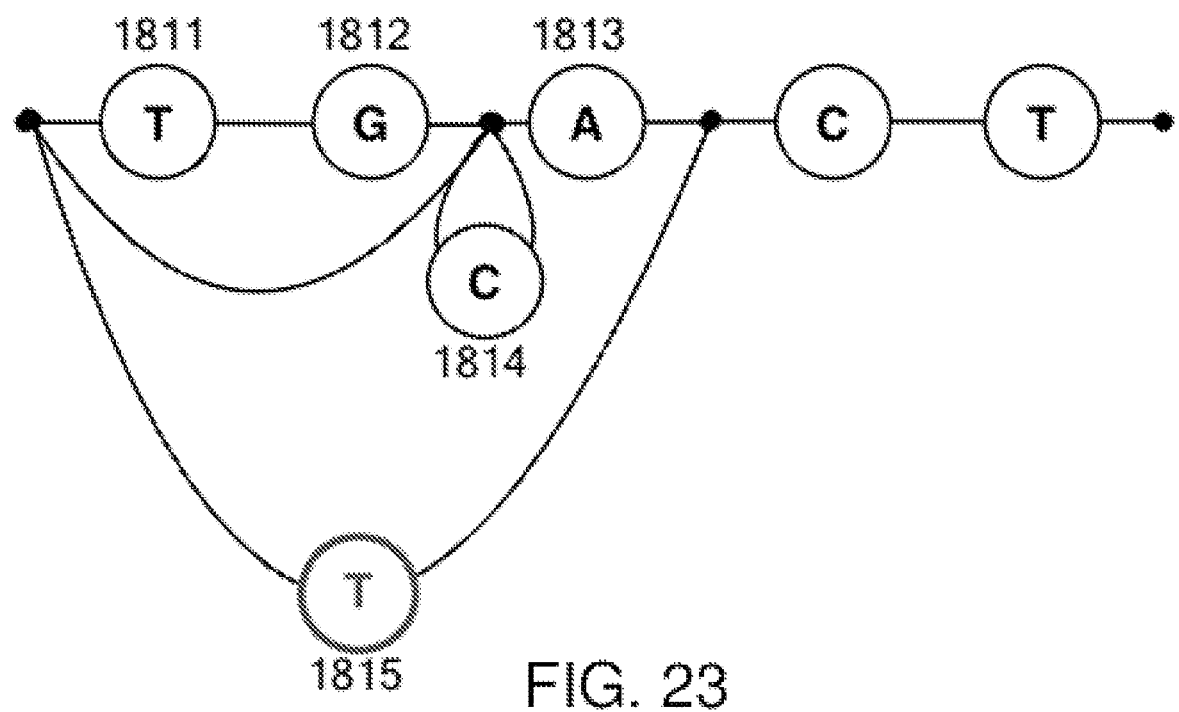
FIG. 23 shows the addition of a nucleotide to the final edge of the DAG.

In particular, the content may be read sequentially from the graph content container and added to the edges in the graph in the order in which they were created. FIG. 21 shows the nucleotides T, G, and A being added to the three edges 1811, 1812, 1813 that were added in a prior step with the second branch 1852. As the third branch 1853 does not have any edges, no content is added. FIG. 22 shows the addition of a C nucleotide to the edge 1814 of the fourth branch 1854. FIG. 23 shows the addition of a T nucleotide to the edge 1815 of the fifth branch 1855. As there are no remaining edges lacking content (and the content container 1143 is empty), the graph 1801 has been deserialized and is now complete.

While in this embodiment, the content is added to the edges once the graph is complete, in other embodiments, content may be added to each branch as it is created. For example, one could add the nucleotides "T, G, A" to vertices 1811, 1812, 1813 once they have been added to the graph, rather than doing so in order once the geometry 1801 of the graph is complete. Similarly, in certain embodiments, the "N" parameter in sequence A may be omitted, as this information can be inferred based on the number of nucleotides present in sequence B. In still further embodiments, the graph geometry and content containers 1139, 1143 could be combined into a single container. For example, each first and second lines of the single container could contain statements describing the geometry and content, respectively, of a branch. Various embodiments are considered to be within the scope of the disclosure.

In this deserialization operation, the graph is built in a memory subsystem of a computer, such as the memory 475 of the computer 433 of FIG. 4. The graph is a clone of the original in that it exhibits the same topology and content as the original. However, any "under the hood" hardware-specific features are implemented in regards to the new location by the deserialization/clone building process.

Thus, where the original genomic graph used physical memory addressing (e.g., through the use of native pointers or index free adjacency as discussed above) specific to the original location of that graph, the clone will use physical memory addressing specific to the new location where the clone is created. The serialization and deserialization process just described was described in a manner applicable to graphs in general, with nucleotide sequence data being merely an example. Thus those operations are equally applicable to other graphs such as suffix and prefix trees, gene ontologies, protein interaction networks, phylogenetic trees and other trees, and any other graph structure.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of serializing biological data, the method comprising:
    representing a plurality of genomic sequences as a graph data structure in a memory subsystem within a computer system, the graph data structure encoding a directed graph representing variability in the plurality of genomic sequences and comprising information specifying a plurality of vertices and a plurality of edges, the plurality of edges connecting the plurality of vertices to form a plurality of paths, such that each of the plurality of genomic sequences is represented by at least one path through the directed graph encoded by the graph data structure; and
    serializing the graph data structure to obtain a serialized graph data structure, the serializing comprising:
        for each of multiple branches in the directed graph,
            generating coordinates for the particular branch, the coordinates comprising a starting coordinate indicating a starting location for a particular branch in the directed graph, an ending coordinate indicating an ending location for the particular branch in the directed graph, and a number of vertices in the particular branch; and
            encoding, into a respective stream of bytes, the coordinates for the particular branch and sequence data for the particular branch;
        wherein the coordinates for the particular branch comprise a tuple of multiple values including:
            a first value indicating a number of edges traversed to reach a particular vertex of the plurality of vertices, wherein at least one traversed edge comprises a branching point; and
            a second value indicating a branch of a set of branches at the branching point.

2. The method of claim 1, wherein the directed graph encoded by the graph data structure is a directed acyclic graph (DAG).

3. The method of claim 2, wherein the graph data structure comprises an adjacency list comprising at least one pointer that indicates at least one location of at least one object adjacent to a first object in the DAG.

4. The method of claim 2, wherein portions of the plurality of genomic sequences that match each other when aligned are represented by a common object in the DAG.

5. The method of claim 1, further comprising:
    deserializing the serialized graph data structure into a clone at least in part by creating a second directed graph comprising the particular branch the first path of the plurality of paths and the sequence data for the particular branch associated with the first path.

6. A system for serializing biological data stored in a graph data structure, the system comprising:
    a processor; and
    a memory subsystem coupled to the processor and storing:
        the graph data structure representing a plurality of genomic sequences, the graph data structure encoding a directed graph representing variability in the plurality of genomic sequences and comprising a plurality of vertices and a plurality of edges, the plurality of edges connecting the plurality of vertices to form a plurality of paths, such that each of the plurality of genomic sequences is represented by at least one path through the directed graph encoded by the graph data structure; and
        instructions, that when executed by the processor, cause the system to serialize the graph data structure to obtain a serialized graph data structure at least in part by:
            for each of multiple branches in the directed graph, generating coordinates for the particular branch, the coordinates comprising a starting coordinate indicating a starting location for a particular branch in the directed graph, an ending coordinate indicating an ending location for the particular branch in the directed graph, and a number of vertices in the particular branch; and encoding, into a respective stream of bytes, the coordinates for the particular branch and sequence data for the particular branch, wherein the coordinates for the particular branch comprise a tuple of multiple values including:

a first value indicating a number of edges traversed to reach a particular vertex of the plurality of vertices, wherein at least one traversed edge comprises a branching point; and a second value indicating a branch of a set of branches at the branching point.

7. The system of claim 6, wherein the directed graph encoded by the graph data structure is a directed acyclic graph (DAG).

8. The system of claim 7, wherein the graph data structure comprises an adjacency list comprising at least one pointer that indicates at least one location of at least one object adjacent to a first object in the DAG.

9. The system of claim 8, wherein portions of the plurality of genomic sequences that match each other when aligned are represented by a common object in the DAG.

10. The system of claim 6, further operable to send the respective first stream of bytes over a network to a computer, wherein the respective first stream of bytes can be deserialized by the computer into a clone within a second memory subsystem of the computer.

11. A method of transferring biological data, the method comprising:

representing a plurality of genomic sequences as a directed acyclic graph (DAG) in a memory subsystem within a computer system, the DAG representing variability in the plurality of genomic sequences and comprising a plurality of vertices and a plurality of edges, the plurality of edges connecting the plurality of vertices to form a plurality of paths, such that each of the plurality of genomic sequences is represented by at least one path through the DAG; and serializing the DAG into a stream of bytes at least in part by:

for each of multiple branches in the DAG, generating coordinates for the particular branch, the coordinates comprising a starting coordinate indicating a starting location for a particular branch in the DAG, an ending coordinate indicating an ending location for the particular branch in the DAG, and a number of vertices in the particular branch, wherein the coordinates for the particular branch comprise a tuple of multiple values including:

a first value indicating a number of edges traversed to reach a particular vertex of the plurality of vertices, wherein at least one traversed edge comprises a branching point; and a second value indicating a branch of a set of branches at the branching point; and encoding, into a respective stream of bytes, the coordinates for the particular branch and sequence data for the particular branch;

deserializing the stream of bytes to identify the coordinates for the particular branch and the sequence data for the particular branch and generating a clone of the DAG that represents the biological data at least in part by modifying a linear graph using the coordinates and the sequence data for the particular branch.

12. The method of claim 1, wherein encoding the first coordinates and sequence data for the particular branch comprises:

appending the coordinates to a first container and appending the sequence data for the particular branch to a second container.

13. The method of claim 1, wherein the starting coordinate and the ending coordinate each indicates a number of vertices traversed to reach a designated edge.

\* \* \* \* \*

UNITED STATES PATENT AND TRADEMARK OFFICE
CERTIFICATE OF CORRECTION

| | |
|---|---|
| PATENT NO. | : 11,347,704 B2 |
| APPLICATION NO. | : 14/885192 |
| DATED | : May 31, 2022 |
| INVENTOR(S) | : Vladimir Semenyuk |

It is certified that error appears in the above-identified patent and that said Letters Patent is hereby corrected as shown below:

In the Claims

At Column 26, Claim 5, Lines 43-45, the text "comprising the particular branch the first path of the plurality of paths and the sequence data for the particular branch associated with the first path." should read -- comprising the particular branch and the sequence data for the particular branch. --.

At Column 27, Claim 10, Lines 28-29, the text "respective first stream of bytes over a network to a computer wherein the respective first stream of bytes" should read -- respective stream of bytes over a network to a computer wherein the respective stream of bytes --.

At Column 28, Claim 12, Line 31, the text "The method of claim 1, wherein encoding the first" should read -- The method of claim 1, wherein encoding the --.

Signed and Sealed this
Twenty-third Day of August, 2022

Katherine Kelly Vidal
*Director of the United States Patent and Trademark Office*